United States Patent
Poulain et al.

(10) Patent No.: US 10,307,410 B2
(45) Date of Patent: Jun. 4, 2019

(54) MCL-1 MODULATING COMPOUNDS FOR CANCER TREATMENT

(71) Applicants: CENTRE REGIONAL DE LUTTE CONTRE LE CANCER FRANCOIS BACLESSE, Caen (FR); UNIVERSITE DE CAEN BASSE-NORMANDIE, Caen (FR); INSTITUT DE CANCEROLOGIE DE L'OUEST RENE GAUDUCHEAU, Saint Herblain (FR)

(72) Inventors: Laurent Poulain, Bretteville l'Orgueilleuse (FR); Anne-Sophie Voisin-Chiret, Bernieres sur Mer (FR); Jana Sopkova-de Oliveira Santos, Cairon (FR); Ronan Bureau, Villers Canivet (FR); Grégory Burzicki, Mericourt (FR); Marcella De Giorgi, Poggiardo (IT); Serge Perato, Luc sur Mer (FR); Jade Fogha, Arcueil (FR); Sylvain Rault, Moult (FR); Philippe Juin, Nantes (FR); Fabien Gautier, Angers (FR)

(73) Assignees: CENTRE REGIONAL DE LUTTE CONTRE LE CANCER FRANCOIS BACLESSE, Caen (FR); UNIVERSITE DE CAEN BASSE-NORMANDIE, Caen (FR); INSTITUT DE CANCEROLOGIE DE L'OUEST RENE GAUDUCHEAU, Saint Herblain (FR)

( * ) Notice: Subject to any disclaimer, the term of this patent is extended or adjusted under 35 U.S.C. 154(b) by 0 days.

(21) Appl. No.: 15/122,890

(22) PCT Filed: Mar. 3, 2015

(86) PCT No.: PCT/IB2015/051553
§ 371 (c)(1),
(2) Date: Aug. 31, 2016

(87) PCT Pub. No.: WO2015/132727
PCT Pub. Date: Sep. 11, 2015

(65) Prior Publication Data
US 2017/0071921 A1    Mar. 16, 2017

(30) Foreign Application Priority Data
Mar. 4, 2014  (EP) .................... 14305309

(51) Int. Cl.
| | | |
|---|---|---|
| A61K 31/444 | (2006.01) | |
| A61K 31/506 | (2006.01) | |
| C07D 401/14 | (2006.01) | |
| C07D 409/14 | (2006.01) | |
| C07D 213/22 | (2006.01) | |
| C07D 213/30 | (2006.01) | |
| C07D 213/55 | (2006.01) | |
| C07D 213/57 | (2006.01) | |
| C07D 213/58 | (2006.01) | |

(52) U.S. Cl.
CPC .......... *A61K 31/444* (2013.01); *A61K 31/506* (2013.01); *C07D 213/22* (2013.01); *C07D 213/30* (2013.01); *C07D 213/55* (2013.01); *C07D 213/57* (2013.01); *C07D 213/58* (2013.01); *C07D 401/14* (2013.01); *C07D 409/14* (2013.01)

(58) Field of Classification Search
None
See application file for complete search history.

(56) References Cited

U.S. PATENT DOCUMENTS

| | | | | |
|---|---|---|---|---|
| 6,603,007 B1 * | 8/2003 | Shintou | ................ | C07D 213/22 546/257 |
| 8,168,307 B2 * | 5/2012 | Iida | ...................... | C07D 209/86 313/504 |
| 8,592,457 B2 * | 11/2013 | Bergman | ............. | C07D 213/81 514/256 |
| 2012/0225851 A1 | 9/2012 | Cardone et al. | | |

FOREIGN PATENT DOCUMENTS

WO    WO 2014/079364    * 11/2013    ........... A61K 31/496

OTHER PUBLICATIONS

Santos, Jana Sopkova-de Oliveira. Structural Characterizations of Oligopyridyl Foldamers, α-Helix Mimetics. Journal of Chemical Information and Modeling. 52 (2012) 429-439.*
Voisin-Chiret, Anne Sophie. A general synthesis of halo-oligopyridines. The Garlanding concept. Tetrahedron. 65(2009) 607-612.*
Voisin-Chiret, Anne Sophie. Aromatic garlands, as new foldamers, to mimic protein secondary structure. Tetrahedron. 68 (2012), 4381-4389.*
Perato., Serge. Synthesis of new linear poly(phenylpyridyl) chains. Tetrahedron. 68 (2012) 1910-1917.*
Constable, Edwin C. Diversification of ligand families through ferroin-neocuproin metal-binding domain manipulation. The Royal Society of Chemistry. (2009) 4918-4927.*
Lin, Yong-Yue. Structural, Photophysical, and Electrophosphorescent Properties of Platinum(ii) Complexes Supported by Tetradentate N2O2 Chelates. Chem. Eur. J. 2003, 9(6), 1264-1272.*
Constable, Edwin C. Cinnamil—an oligopyridine precursor. Tetrahedron Letters. 1994, 35(36), 6657-6660.*

(Continued)

*Primary Examiner* — Samantha L Shterengarts
(74) *Attorney, Agent, or Firm* — Duane Morris LLP; Gregory M. Lefkowitz; Jason M. Nolan

(57) ABSTRACT

The invention relates to compounds of formula (I), and to their therapeutic use in the treatment of cancer:

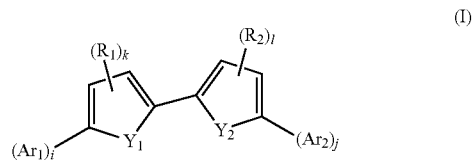

Wherein $Y_1$, $Y_2$, $Ar_1$, $Ar_2$, $R_1$, $R_2$, i, j, k, l are as defined in claim 1.

18 Claims, 4 Drawing Sheets

Specification includes a Sequence Listing.

(56) References Cited

OTHER PUBLICATIONS

Voisin-Chiret et al.: "A general synthesis of halo-oligopyridines. The Garlanding concept", Tetrahedron, vol. 65, No. 3, Jan. 17, 2009 (Jan. 17, 2009), pp. 607-612, XP025780052, ISSN: 0040-4020, [retrieved on Nov. 13, 2008], DOI: 10.1016/J.TET.2008 .11.024.

Burzicki et al.: "Synthesis of New [2,3':6',3"]Terpyridines Using Iterative Cross-Coupling Reactions", Synthesis, vol. 2010, No. 16, Aug. 1, 2010 (Aug. 1, 2010) pp. 2804-2810, XP055115908, ISSN: 0039-7881, DOI: 10.1055/s-0030-1258147.

Voisin-Chiret et al.: "Synthesis of new phenylpyridyl scaffolds using the Garlanding approach", Tetrahedron, vol. 66, No. 40, Oct. 2, 2010 (Oct. 2, 2010), pp. 8000-8005, XP027263352, ISSN: 0040-4020, [retrieved on Aug. 12, 2010].

Voisin-Chiret et al.: "Aromatic garlands, as new foldamers, to mimic protein secondary structure", Tetrahedron, vol. 68, No. 23, Feb. 14, 2012 [Feb. 14, 2012], pp. 4381-4389, XP028483000. ISSN:0040-4020, [retrieved on Mar. 3, 2012], DOI: 10.1016/J.TET. 2012.02.035.

Perato et al.: "Synthesis of new linear poly(phenylpyridyl) chains", Tetrahedron, vol. 68, No. 7, Dec. 28, 2011 [Dec. 28, 2011], pp. 1910-1917, XP028453879, ISSN: 0040-4020, [retrieved on Jan. 4, 2012], DOI: 10-1016/J.TET.2011.12.074.

Sopkova-de Oliveira Santos et al.: "Structural Characterizations of Oligopyridyl Foldamers, [Alpha]-Helix Mimetics", Journal of Chemical Information and Modeling, vol. 52, No. 2, Feb. 27, 2012 (Feb. 27, 2012), pp. 429-439, XP055146587 , ISSN: 1549-9596, DOI: 10.1021/ci200424a.

Cohen et al.: "A Competitive Stapled Peptide Screen Identifies a Selective Small Molecule that Overcomes MCL-1-Dependent Leukemia Cell Survival", Chemistry & Biology, vol. 19, No. 9, Sep. 1, 2012 (Sep. 1, 2012), pp. 1175-1186, XP055147153, ISSN: 1074-5521, DOI: 10.1016/j.chembiol.2012.07.018.

Wei et al.: "Chemical Genomics Identifies Small-MoleculeRepressors and BCL-xL as a Predictor of MCL1 Dependency", Cancer Cell, vol. 21, No. 4, Feb. 27, 2012 (Feb. 27, 2012), pp. 547-562, XP028410930, ISSN: 1535-6108, [retrieved on Mar. 19, 2012], DOI: 10.1016/J.CCR.2012.02.028.

Gloaguen et al.: "First Evidence That Oligopyridines, [Alpha]-Helix Foldamers, Inhibit Mcl-1 and Sensitize Ovarian Carcinoma Cells to Bcl-x L—Targeting Strategies", J. Med. Chem., vol. 28, No. 4, Jan. 13, 2015 (Jan. 13, 2015), pp. 1644-1668, XP055202086, ISSN:0022-2623, DOI:10.1021/jm500672y.

* cited by examiner

MCL-1 MODULATING COMPOUNDS FOR CANCER TREATMENT

CROSS-REFERENCE TO RELATED APPLICATIONS

This application is a § 371 national stage entry of International Application No. PCT/IB2015/051553, filed Mar. 3, 2015, which claims priority to European Patent Application No. 14305309.8 filed Mar. 4, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 5, 2016, is named F9057-11801-F6234-05605_SL.txt and is 1,454 bytes in size.

The present invention relates to compounds, compositions and methods for treating cancers and disorders of cell proliferation and more particularly, methods of making and using compounds that modulate Mcl-1; said compounds may be contained in pharmaceutical compositions and used as therapeutic agents.

Cancer is a leading cause of death worldwide. Apoptosis, also known as programmed cell death, is a natural process used by multicellular organisms to eliminate aging or damaged cells also involved in various physiological processes such as morphogenesis and tissue homeostasis. Apoptosis is a complex, highly regulated process involving many proteins. Some of these proteins promote cell death ("pro-apoptotic" proteins) and some prevent it ("anti-apoptotic" proteins). Cancer cells tend to over-express anti-apoptotic genes. The over-expression of anti-apoptotic genes is associated with tumor formation, metastatic growth and resistance to chemotherapy and there is a continuing need for therapeutic strategies that selectively kill cancer cells.

More specifically, apoptosis control defect is frequently involved in chemoresistance in cancer cells, in both hematological malignancies and solid tumors, and the deregulation of Bcl-2 family members expression constitutes one of the most frequent and important event. These proteins share Bcl-2 homology domains (named BH domains). Anti-apoptotic proteins (Bcl-2, Bcl-$x_L$ ... ) contain the BH1 to BH4 domains, whereas pro-apoptotic proteins contain either the BH1 to BH3 domains (multidomain members such as Bax and Bak) or only the BH3 domain (BH3-only group such as Bim, Puma, Bid, Bad, Noxa and Hrk) (Adams, J. M. and Cory, S. (2007) *Oncogene* 26, 1324-1337). Under cellular stress, BH3-only proteins initiate apoptosis by either blocking the activity of anti-apoptotic members or directly activating multidomain pro-apoptotic members, which is mediated via interaction of the BH3 domain of one protein with the hydrophobic pocket of another (Shamas-Din et al. (2011) *Biochimica et Biophysica Acta* 1813, 508-520).

Constant efforts are made to impede the activity of anti-apoptotic members such as Bcl-2 or Bcl-$x_L$, among which the development of potent BH3-mimetic molecules represent a promising way. These molecules bind to the BH3-binding groove in anti-apoptotic proteins of the Bcl-2 family and promote cell death through the release of pro-apoptotic Bcl-2 family members (Zhang, Lin et al. (2007) *Drug Resist. Updat.* 10, 207-217). ABT-737 (and the orally available compound related to ABT-737, ABT-263 or Navitoclax) allows an efficient inhibition of the anti-apoptotic activity of Bcl-2 and Bcl-$x_L$. It has been shown as able to induce apoptotic cell death as a single agent in hematologic malignancies and, to a lower extent, in solid tumor cells. ABT-737 can also sensitize cancer cells to chemotherapy. However, its activity has been conditioned to the absence or to the inactivation of Mcl-1, whereas the strong expression and activity of Mcl-1 is associated to the absence of response to ABT-737 (Dai, Y. and Grant, S. (2007) *Cancer Res.* 67(7), 2908-2911). The expression and activity of the anti-apoptotic protein Mcl-1 thus constitutes a major hurdle for the activity of ABT-737.

In ovarian carcinoma, inventors previously demonstrated that Bcl-$x_L$ and Mcl-1 cooperate to protect tumor cells against apoptosis, and that their concomitant inhibition leads to massive apoptosis even in absence of chemotherapy, whereas the down-regulation of either Bcl-$x_L$ or Mcl-1 remains ineffective (Brotin et al. (2010) *Int J Cancer* 126, 885-895). In this context, they also showed that Mcl-1 down regulation or inactivation was required to sensitize ovarian cancer cells to Bcl-$x_L$-targeting BH3-mimetic molecules such as HA14-1 (Simonin et al. (2009) *Mol Cancer Ther* 8, 3162-3170) or ABT-737 (Simonin et al. (2013) *Apoptosis* 18, 492-508).

Mcl-1 contains three BH domains (BH1-BH3) but lacks a clearly defined BH4 domain at the $NH_2$ terminus. Mcl-1 localizes to various intracellular membranes, especially, the outer mitochondrial membrane through a transmembrane domain at its COOH terminus. Like Bcl-2 and Bcl-$x_L$, Mcl-1 can interact with Bax and/or Bak to inhibit mitochondria-mediated apoptosis. Unlike Bcl-2 and Bcl-$x_L$, Mcl-1 expression is quickly induced upon exposure to cytokines or growth factors. Increased Mcl-1 expression promotes cell viability in a wide range of tumor cell types, including leukemias, hepatocellular carcinomas, melanoma, prostate and breast cancer cells. Moreover, Mcl-1 plays a role in cell immortalization and tumorigenesis in many kinds of cancers through amplification of somatic copy number. Cancer cells harboring Mcl-1 amplification are frequently dependent upon Mcl-1 for survival. (Beroukhim, R. et al. (2010) *Nature* 463, 899-905).

Mcl-1 is overexpressed in various tumor cells, including ovarian carcinoma, and its expression has also been associated to chemoresistance (Shigemasa et al. (2002) *Jpn J Cancer Res* 93, 542-550). Importantly, Mcl-1 locus is one of the most frequently amplified in human cancers, further pointing to its centrality in carcinogenesis and increasing its importance as a high priority therapeutic target (Beroukhim et al. (2010) *Nature* 463, 899-905).

Various tools aiming at inhibiting Mcl-1 have thus been used to sensitize ABT-737 such as:

Mcl-1-targeting siRNA (Lin et al. (2007) *Oncogene* 26, 3972-3979),

Noxa gene transfer (Wesarg et al. (2007) *Int J Cancer* 121, 2387-2394; Lucas et al. (2012) *Clin Cancer Res* 18, 783-795), signaling pathways inhibition (Russo et al. (2013) *Biochem Pharmacol* 85, 927-936), or conventional chemotherapy (Mason et al. (2009) *Leukemia* 23, 2034-2041; Simonin et al. (2013) *Apoptosis* 18, 492-508).

These strategies either lead to the inhibition of Mcl-1 expression itself, or to the indirect inhibition of its anti-apoptotic activity through the activation of its endogenous inhibitors, i.e. BH3-only proteins such as Bim, Noxa or Puma. As previously demonstrated, platinum compounds-based chemotherapy is thus able to decrease Mcl-1 protein level as well as to induce BH3-only proteins in ovarian carcinoma, leading to a sensitization to ABT-737 (Simonin et al. (2009) *Molecular Cancer Therapeutics*, 8(11), 3162-70 and Simonin et al. (2013) *Apoptosis* 18, 492-508). However, the difficult application of such strategies in clinical practice, in part due to cumulative toxicities (conventional chemotherapies) or to In vivo inefficiency (siRNA, gene therapy), incites researchers to identify specific and potent Mcl-1 inhibitors.

Accordingly, it is an object of the present invention to provide alternative compounds useful for modulating, notably inhibiting, Mcl-1 activity.

The present invention is thus directed, in one aspect, to various compounds of structure:

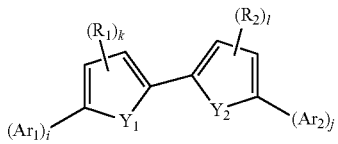

or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt thereof.

Another object of the present invention is to provide a combination of compounds of formula (I) with Bcl-2 or Bcl-$x_L$ inhibitors.

Another object of the present invention is to provide compounds of formula (I) for use in the treatment of cancer.

Another object of the present invention is to provide a method of preparation of compounds of formula (I) and specific compounds of formula (IIa) or (IIb) useful for the preparation of compounds of formula (I).

These and other objects, features and advantages of the compounds of formula (I) will be disclosed in the following detailed description of the patent disclosure.

Compounds of Formula (I)

In a first object, the present invention provides compounds of formula (I):

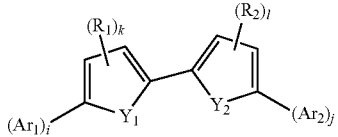

Wherein:

$Y_1$, $Y_2$ are each independently selected from —S—, —C=C—, —N=C—, provided that when one of $Y_1$, $Y_2$ is —S— then the other one is —N=C—;

$Ar_1$, $Ar_2$ are each independently selected from a $C_6$-$C_{10}$ aryl or a 5 to 7 membered heteroaryl, said aryl and heteroaryl groups being optionally substituted by one to three $R_3$ groups provided that:

$Ar_1$, $Ar_2$ cannot both represent a same group selected from a 4-pyridyl, an unsubstituted 2 or 3-thiophenyl, a 3,4-dimethoxyphenyl or a 3,4,5-trimethoxyphenyl, i and j are independently 0 or 1, provided that:
i+j≥1; and
when none of $Y_1$, $Y_2$ is —S—, then i+j=2;

$R_1$, $R_2$, are at each occurrence, independently selected from, $C_1$-$C_6$ alkyl, $C_6$-$C_{10}$ aryl, ($C_6$-$C_{10}$)aryl($C_1$-$C_6$)alkyl, ($C_6$-$C_{10}$)aryl($C_2$-$C_6$)alkenyl, ($C_6$-$C_{10}$)arylcarbonyl, ($C_6$-$C_{10}$)aryl($C_1$-$C_6$)alkylcarbonyl, C(=O)H, COOH, OH said alkyl groups being optionally substituted by OH;

k and l are independently 0, 1;

$R_3$ is, at each occurrence, independently selected from $C_1$-$C_6$ alkyl, $C_1$-$C_6$ alkoxy, OH, C(=O)H, $(CH_2)_nCO_2H$, $(CH_2)_pCN$, $(CH_2)_qC(=N(OH))NH_2$, I, Cl, Br, F, $C_6$-$C_{10}$ aryl, and a 5 to 7 membered heteroaryl, ($C_6$-$C_{10}$)aryl($C_1$-$C_6$)alkyl, ($C_6$-$C_{10}$)aryl($C_2$-$C_6$)alkenyl, said alkyl groups being optionally substituted by OH;

n is 0, 1, 2, 3;
p is 0, 1, 2, 3;
q is 0, 1, 2, 3;

with the exclusion of the following compounds:
2-(pyridin-3-yl)-5-(5-(pyridin-3-yl)-3-styrylpyridin-2-yl)pyridine
3-(5-methyl-6-(5-methyl-6-(pyridin-3-yl)pyridin-3-yl)pyridin-3-yl)pyridine
3-(6-(5-methyl-6-(pyridin-3-yl)pyridin-3-yl)pyridin-3-yl)pyridine
and the pharmaceutically acceptable salts thereof.

In certain aspects, there are included compounds of formula (I) wherein both $Y_1$ and $Y_2$ are —N=C—.

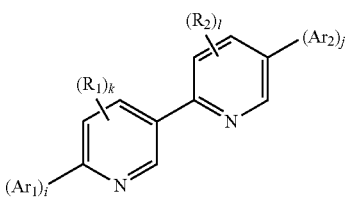

In a particular aspect, there are included compounds of formula (I) wherein $Ar_1$, $Ar_2$ are as defined above, provided that at least one of $Ar_1$, $Ar_2$ is a 5 to 7 membered heteroaryl.

In another aspect, there are included compounds of formula (I), wherein when both $Y_1$ and $Y_2$ are —N=C—, then at least one of $Ar_1$, $Ar_2$ is phenyl.

In another aspect, there are included compounds of formula (I) wherein $Ar_1$ and/or $Ar_2$ are selected from phenyl, pyridyl, pyrimidyl, imidazolyl, pyrazolyl, thiophenyl, triazolyl, in particular from phenyl, 3-pyridyl, 5-pyrimidyl, 2-imidazolyl, 3-pyrazolyl, 2-thiophenyl, 4-triazolyl.

In yet another aspect, there are included compounds of formula (I) wherein at least one of $Ar_1$, $Ar_2$ is a 5 to 7 membered heteroaryl containing a nitrogen atom, preferably pyridyl, notably 3-pyridyl.

In still another aspect, there are included compounds of formula (I) wherein $Ar_1$ is 3-pyridyl or phenyl.

In another aspect, there are included compounds of formula (I) wherein $Ar_2$ is 3-pyridyl or phenyl.

In certain aspect, there are included compounds of formula (I) wherein $R_1$, $R_2$ are independently selected from $C_1$-$C_6$ alkyl, ($C_6$-$C_{10}$)aryl($C_2$-$C_6$)alkenyl, preferably from methyl and styryl.

In another aspect, there are included compounds of formula (I) wherein $R_1$ is 5-methyl.

In yet another aspect, there are included compounds of formula (I) wherein $R_2$ is 5-styryl.

In a preferred aspect, there are included compounds of formula (I) wherein $R_1$ is 5-methyl and $R_2$ is 5-styryl.

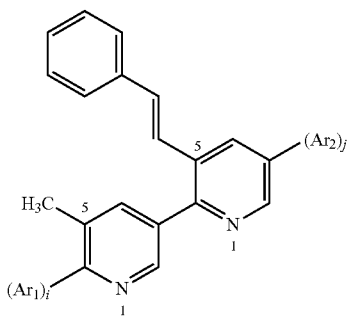

(I)

In another aspect, there are included compounds of formula (I) wherein $Y_1$ is —S— and $Y_2$ is —N=C—.

In still a certain aspect, there are included compounds of formula (I) wherein $Ar_1$ is a 5 to 7 membered heteroaryl, in particular pyridyl, more particularly 3-pyridyl.

In yet a certain aspect, there are included compounds of formula (I) wherein $Ar_1$ is substituted by a 5 to 7 membered heteroaryl, in particular thiophenyl, more particularly 3-thiophenyl.

In still another aspect, there are included compounds of formula (I) wherein $Ar_2$ is a 5 to 7 membered heteroaryl, in particular pyridyl or thiophenyl, more particularly 3-pyridyl, 2-thiophenyl or 3-thiophenyl.

In other aspects, there are included compounds of formula (I) wherein $R_1$ is selected from $C_1$-$C_6$ alkyl, ($C_6$-$C_{10}$)aryl ($C_1$-$C_6$)alkyl, notably from methyl, isopropyl, or naphtyl-$CH_2$—.

In other aspects, there are included compounds of formula (I) wherein the pharmaceutically acceptable salts are hydrochloride salts.

In other aspects, there are included compounds of formula (I) selected from the compounds of formula (Ia), (Ib), (Ic) and (Id):

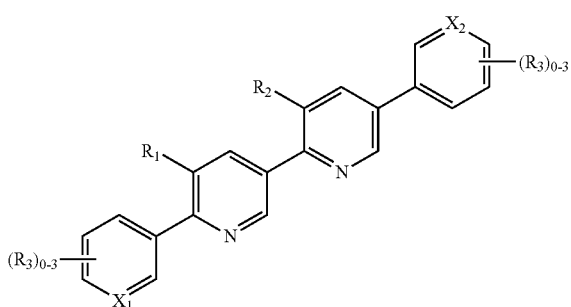

(Ia)

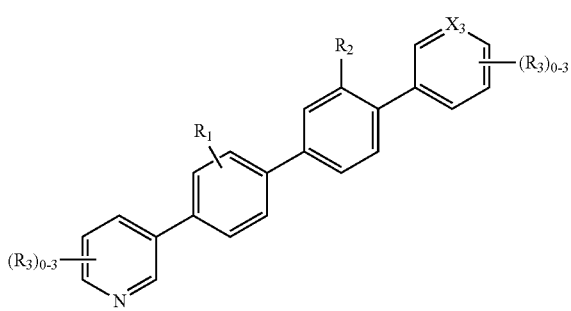

(Ib)

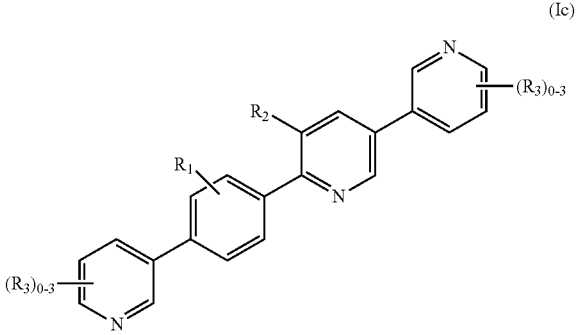

(Ic)

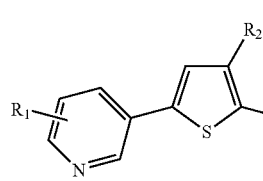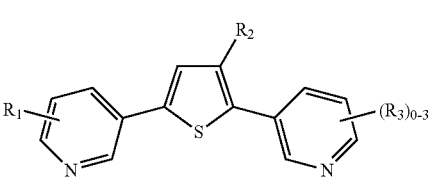

(Id)

Wherein:

$X_1$, $X_2$, $X_3$, are at each occurrence, independently selected from C or N;

$R_1$, $R_2$, $R_3$ are independently, at each occurrence, as defined above.

In still other aspects, there are included compounds of formula (I) which are selected from:
- 5,6'-di(pyridin-3-yl)-5'-methyl-3-((E)-styryl)-2,3'-bipyridine (MR29072)
- 5,6"-di(pyridin-3-yl)-3,5"-bis-((E)-styryl)-[2,3';6',3"] terpyridine (MR29075)
- 3,5",5'-trimethyl-5,6"-diphenyl-[2,3';6',3"]-terpyridine (MR30802)
- 5'-bromo-3',5-dimethyl-6-(3-methyl-4-pyridin-3-yl)-3,2'-bipyridine (MR30804)
- 5'(2-methyl-4-pyridin-3-ylphenyl)-3',5-dimethyl-6-(2-methyl-4-pyridin-3-ylphenyl)-3,2'-bipyridine (MR30811)
- 2-(pyridin-3-yl)-5-(3-methyl-4-pyridin-3-ylphenyl)-(E) styrylbenzene (MR 30820)
- 3-(4-methyl-5-(pyridine-3-yl)thiophen-2-yl)pyridine (MR31327)
- 3-(4-((naphtalen-3-yl)methyl)-5-(pyridine-3-yl)thiophen-2-yl)pyridine (MR31328)
- 3-(4-isobutyl-5-(pyridine-3-yl)thiophen 2-yl)pyridine (MR31330)
- 2-(5-methyl-6-(pyridin-3-yl)pyridin-3-yl)-5-phenyl-3-styrylpyridine (MR31348)
- 2-(5-methyl-6-phenylpyridin-3-yl)-5-(pyridin-3-yl)-3-styrylpyridine (MR31349)
- 5-(3-benzylpyridin-2-yl)-2-(5-benzylpyridin-3-yl)pyridine (MR31397)

and pharmaceutically acceptable salts thereof.

In preferred aspects, the compound of formula (I) is:
- 5,6'-di(pyridin-3-yl)-5'-methyl-3-((E)-styryl)-2,3'-bipyridine (MR29072)

and its hydrochloride salts.

Method of Preparation of Compound of Formula (I)

The compounds of the present invention may be prepared in a number of methods well known to those skilled in the art, including, but not limited to those described below, or through modifications of these methods by applying standard techniques known to those skilled in the art of organic synthesis. The reagents and starting materials are commercially available, or readily synthesized by well-known techniques by one of ordinary skill in the arts. All substituents, unless otherwise indicated, are as previously defined. All processes disclosed in association with the present invention are contemplated to be practiced on any scale, including milligram, gram, multigram, or commercial industrial scale.

As will be readily understood, functional groups present on the compounds of Formula I may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Other preferred protecting groups according to the invention may be found in Greene, T. W. and Wuts, P. G. M., "Protective Groups in Organic Synthesis" 2d. Ed., Wiley & Sons, 1991, or in P. J. Kocienski, "Protecting Groups", 3$^{rd}$. Ed., Thieme, Stuttgart, N.Y., 2004.

The compound thus prepared may be recovered from the reaction mixture by conventional means. For example, the compounds may be distilled off from the solvent mixture after the extraction or, if necessary after distilling off from the solvent mixture, pouring the residue into water followed by extraction with a water-immiscible organic solvent and distilling off from the solvent mixture. Additionally, the product can, if desired, be further purified by various well known techniques, such as recrystallization, precipitation or the various chromatography techniques, notably column chromatography or preparative thin layer chromatography, in particular High Performance Liquid Chromatography (HPLC).

In another object, the present invention relates to a method for preparing a compound of formula (I) as defined herein, comprising the steps of:

i) reacting a compound (IIa) with Ar$_2$B(OH)$_2$ in the presence of a palladium (Pd$^0$) catalyst and a base according to a Suzuki-Miyaura coupling;

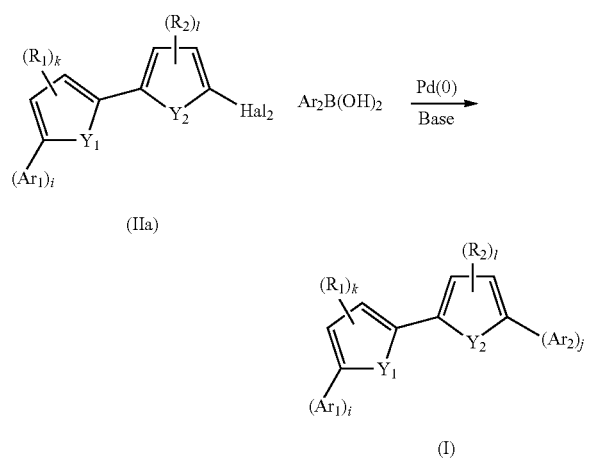

(IIa)

(I)

wherein Y$_1$, Y$_2$, Ar$_1$, Ar$_2$, R$_1$, R$_2$, i, j, k, l are as defined above, and Hal$_2$ is I or Br; and optionally ii) recovering the obtained compound of formula (I).

In a further aspect, the compound of formula (IIa) is prepared according to a process comprising the steps of:

i) reacting a compound of formula (IV) with boronic acid (III) in the presence of a palladium (Pd$^0$) catalyst and a base according to a Suzuki-Miyaura coupling;

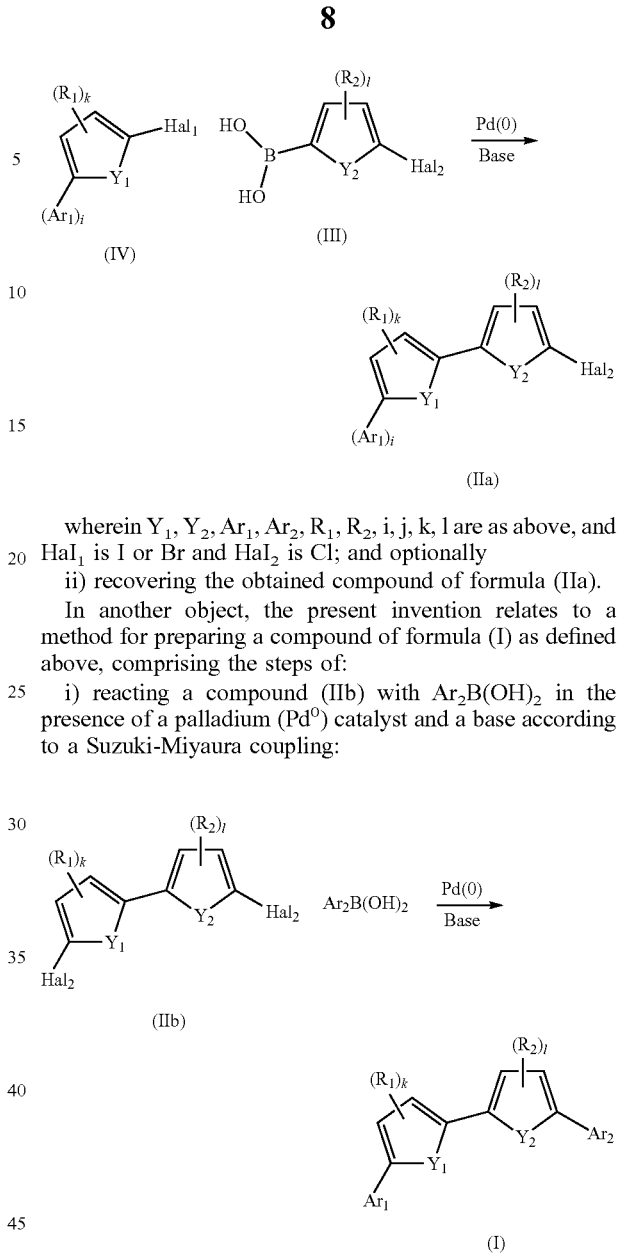

wherein Y$_1$, Y$_2$, Ar$_1$, Ar$_2$, R$_1$, R$_2$, i, j, k, l are as above, and Hal$_1$ is I or Br and Hal$_2$ is Cl; and optionally ii) recovering the obtained compound of formula (IIa).

In another object, the present invention relates to a method for preparing a compound of formula (I) as defined above, comprising the steps of:

i) reacting a compound (IIb) with Ar$_2$B(OH)$_2$ in the presence of a palladium (Pd$^0$) catalyst and a base according to a Suzuki-Miyaura coupling:

wherein Y$_1$, Y$_2$, Ar$_1$, Ar$_2$, R$_1$, R$_2$, k, l are as defined above, Ar$_1$ and Ar$_2$ being the same, and Hal$_2$ is I or Br, and optionally ii) recovering the obtained compound of formula (I).

Synthetic Intermediates Useful for Preparing the Compounds of Formula (I)

In a further object, the present invention relates to a compound of formula (IIa):

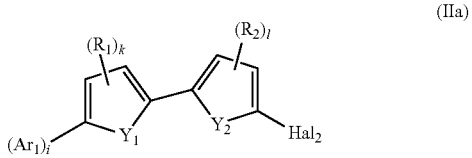

wherein

Y$_1$, Y$_2$, Ar$_1$, Ar$_2$, R$_1$, R$_2$, i, j, k, l are as defined above, and Hal$_2$ is I, Br or Cl.

As an example, the compounds of formula (IIa) may be selected from:

2-(6-bromo-5-methylpyridin-3-yl)-5-(5-chloro-1-methyl-1H-imidazol-2-yl)-3-styrylpyridine (MR31352)

2-bromo-3-methyl-5-(5-(pyridin-3-yl)-3-styrylpyridin-2-yl)pyridine (MR31360)

5-(6-(6-bromo-5-methylpyridin-3-yl)-5-styrylpyridin-3-yl)pyrimidine (MR31362)

3-(6-(6-bromo-5-methylpyridin-3-yl)-5-styrylpyridin-3-yl)phenol (MR31377)

2-(3-(6-(6-bromo-5-methylpyridin-3-yl)-5-styrylpyridin-3-yl)phenyl)acetonitrile (MR31380)

In still a further object, the present invention relates to a compound of formula (IIb):

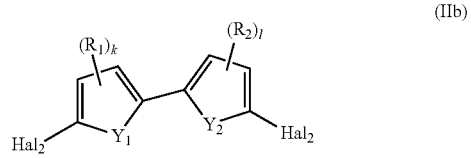

(IIb)

$Y_1, Y_2, Ar_1, Ar_2, R_1, R_2, I, j, k, l$ are as defined above, and $Hal_2$ is I or Br.

As an example, the compounds of formula (IIb) may be selected from:

5-bromo-2-(6-bromo-5-methylpyridin-3-yl)-3-styrylpyridine (MR29061)

5-bromo-2-(6-iodo-5-methylpyridin-3-yl)-3-styrylpyridine (MR29069)

Pharmaceutical Compositions

In another object, the present invention relates to a pharmaceutical composition comprising a compound of formula (I):

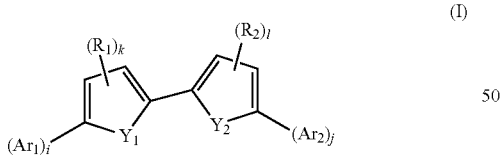

(I)

Wherein $Y_1, Y_2, Ar_1, Ar_2, R_1, R_2, i, j, k$ and $l$ are as defied above, and the pharmaceutically acceptable salts thereof, with the exclusion of the compounds:

2-(pyridin-3-yl)-5-(pyridin-3-yl)-3-styrylpyridin-2-yl)pyridine 3-(5-methyl-6-(5-methyl-6-(pyridin-3-yl)pyridin-3-yl)pyridin-3-yl)pyridine 3-(6-(5-methyl-6-(pyridin-3-yl)pyridin-3-yl)pyridin-3-yl)pyridine in admixture with at least one pharmaceutically acceptable excipient or carrier.

In a particular aspect, there are included pharmaceutical compositions as defined above wherein the following compounds of formula (I) are excluded:

3,3'-dimethyl-2,5"-dipyridin-3-yl-[2,5';2',5"]terpyridine

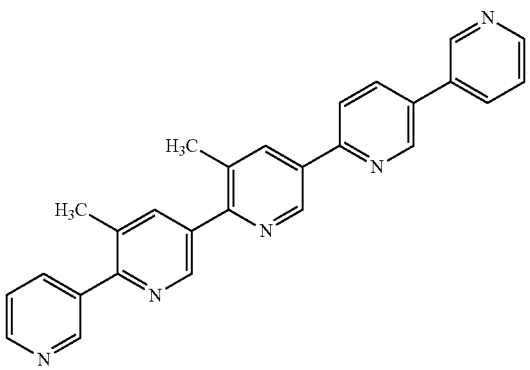 [SMILES: Cc1cc(-c2ccc(-c3cccnc3)cn2)cnc1-c1cnc(-c2cccnc2)c(C)c1]

3,3',3"-triethyl-2,5"-dipyridin-3-yl-[2,5';2',5"]terpyridine

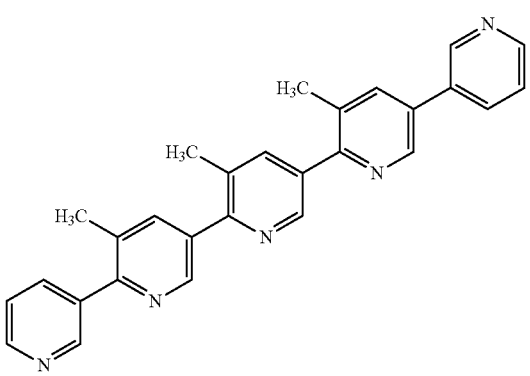 [SMILES: Cc1cc(-c2cccnc2)cnc1-c1cnc(-c2cnc(-c3cccnc3)c(C)c2)c(C)c1]

3,3',3",3'''-tetramethyl-2,5"-dipyridin-3-yl-[2,5';2',5";2",5''']quaterpyridine

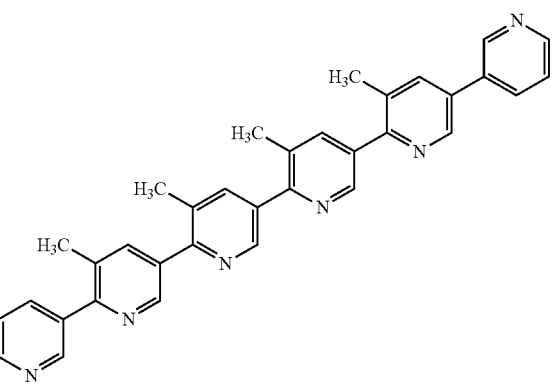 [SMILES: Cc1cc(-c2cccnc2)cnc1-c1cnc(-c2cnc(-c3cnc(-c4cccnc4)c(C)c3)c(C)c2)c(C)c1]

3',3'',3'''-trimethyl-2,5''-dipyridin-3-yl[2,5';2',5'';2''', 5''']quaterpyridine

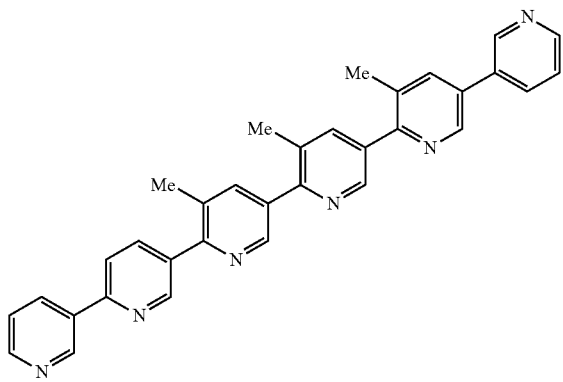 [SMILES: Cc1cc(-c2cccnc2)cnc1-c1cnc(-c2cnc(-c3ccc(-c4cccnc4)nc3)c(C)c2)c(C)c1]

In a particular aspect, there are included pharmaceutical compositions wherein the compounds of formula (I) are as defined above provided that:

when both $Y_1$, $Y_2$ are N=C, or one of $Y_1$, $Y_2$ is N=C and the other is C=C, and both $Ar_1$, $Ar_2$ are pyridinyl, then at least one of $R_1$, $R_2$ is present and is different from H or $CH_3$.

In other aspects, there are included pharmaceutical compositions, further comprising a Bcl-$x_L$ inhibitor, notably a BH3-mimetic inhibitor, such as HA 14-1, ABT-737 or ABT-263.

As will be apparent to one of ordinary skill in the art, the specific formulations of said pharmaceutical composition can be selected based on the type of cancer being treated. The compositions of the invention can be formulated for administration to a patient with materials that improve their stability and/or provide for a controlled or sustained release In vivo.

These pharmaceutical compositions can be prepared in a well known manner in the pharmaceutical art and, can be administered by a variety of routes, depending upon whether local or systemic treatment is desired and upon the area to be treated.

Administration may be topical (including skin, ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration.

The pharmaceutical compositions can be formulated so as to provide quick, sustained or delayed release of the active ingredient after administration to the patient by employing procedures known in the art.

Pharmaceutical compositions usually comprise pharmaceutically acceptable, inorganic or organic carriers, preservatives, solubilizers, stabilizers, wetting agents, emulsifiers, sweeteners, colorants, flavorings, salts for varying the osmotic pressure, buffers, masking agents or antioxidants. They can also contain still other therapeutically valuable substances. These ingredients are selected on the basis of the mode and route of administration. Suitable pharmaceutical ingredients, as well as pharmaceutical necessities for use in pharmaceutical formulations, are described in Remington's Pharmaceutical Sciences (E. W. Martin).

The therapeutic dosage of the compounds of the present invention can vary according to, for example, the particular use for which the treatment is made, the manner of administration of the compound, the health and condition of the patient, and the judgment of the attending clinician. The proportion or concentration of a compound of the invention in a pharmaceutical composition can vary depending upon a number of factors including dosage, chemical characteristics (e.g., hydrophobicity), and the route of administration.

Combinations

In some embodiments, the compounds of the invention may be associated with at least one second therapeutic agent.

The compounds may thus be administered with another therapeutic agent, such as a cytotoxic agent, or cancer chemotherapeutic. Concurrent administration of two or more therapeutic agents does not require that the agents be administered at the same time, during the same period of time or by the same route, as long as there is an overlap in the time period during which the agents are exerting their therapeutic effect. Simultaneous or sequential administration is contemplated, as its administration on different days or weeks.

Other useful therapeutics that may be administered in combination with the present compounds include agents that target other members of the Bcl-2 family. An anti-Bcl-2 agent can be any agent that modulates the activity of Bcl-2 and can include anti-Bcl-2 oligonucleotides, anti-Bcl-2 antibodies and small molecule inhibitors. Exemplary small molecule inhibitors include gossypol and gossypol analogues (e.g., AT-101); the benzenesulfonyl derivative, TW37; the apogossypol derivative, Sabutoclax; the ABT series of compounds including ABT-199, ABT-737 and the orally available analog, ABT-263; Obatoclax; and HA14-1.

The present invention preferably relates to a combination comprising a compound of formula (I) in combination with a Bcl-$x_L$ inhibitor, notably a BH3-mimetic inhibitor, such as HA14-1, ABT-737 or ABT-263.

Compounds of Formula (I) for Use in the Treatment of Cancer

The compounds and compositions disclosed herein are generally and variously useful for treatment of cancer.

In a further object, the present invention thus relates to a compound of formula (I),

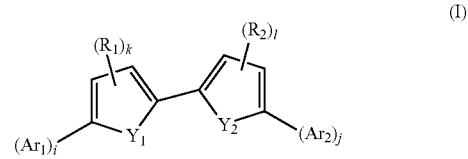

(I)

Wherein:
$Y_1$, $Y_2$, $Ar_1$, $Ar_2$, $R_1$, $R_2$, i, j, k and l are as defined above, and the pharmaceutically acceptable salts thereof,
for use in the treatment of cancer; notably cancers that are responsive to the modulation of Mcl-1.

Cancers amenable to the therapeutic methods of the invention can be cancers that are responsive to the modulation of Mcl-1; any form of cancer which is associated with misregulation of Mcl-1 (e.g., overexpression or altered binding or activity) is thus within the scope of the invention.

Cancers or neoplastic disorders include, for example, without limitation, breast cancer, hematological cancers such as myeloma, leukemia and lymphoma (e.g., Burkitt lymphoma, non-Hodgkin lymphoma, Hodgkin lymphoma, and acute T cell leukemia), neurological tumors such as brain tumors, e.g., gliomas, including astrocytomas or glioblastomas, melanomas, lung cancer, head and neck cancer, thyroid cancer, gastrointestinal tumors such as stomach, colon or rectal cancer, liver cancer, pancreatic cancer, genitourinary tumors such ovarian cancer, vaginal cancer, vulval cancer, endometrial cancer, bladder cancer, kidney cancer, testicular cancer, prostate cancer, or penile cancer, bone tumors, vascular tumors, and skin cancers such as basal cell carcinoma, squamous cell carcinoma and melanoma.

Preferably, compounds of formula (I) are useful for the treatment of hematological malignancies, for example, lymphoma, leukemia, multiple myeloma; and of solid tumors such as ovarian cancers, mesothelioma, melanoma, pancrea, lung, breast, kidney and liver cancers. Hematological malignancies have been described as addicted to Mcl-1 (Dai et al., (2007) Cancer Res., 67(7), 2908-11; Yecies et al., (2010) Blood, 115(16), 3304-13) for the response to Bcl-xL targeting strategies.

In a particular aspect the compounds of formula (I) are administered together with a Bcl-$x_L$ inhibitor, notably a BH3-mimetic inhibitor, such as:

2-Amino-6-bromo-α-cyano-3-(ethoxycarbonyl)-4H-1-benzopyran-4-acetic acid ethyl ester (also named HA 14-1)

HA 14-1

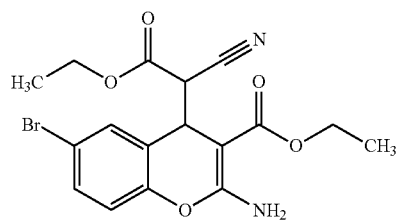

4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide (also named ABT-737)

or

ABT-737

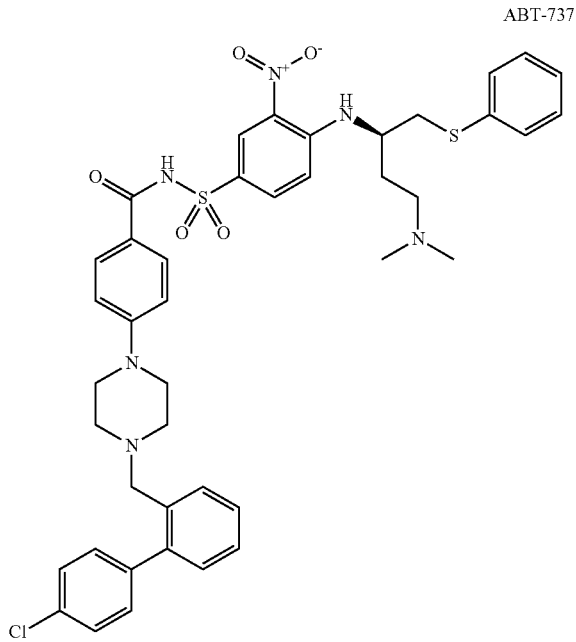 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]

4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide (also named ABT-263)

ABT-263

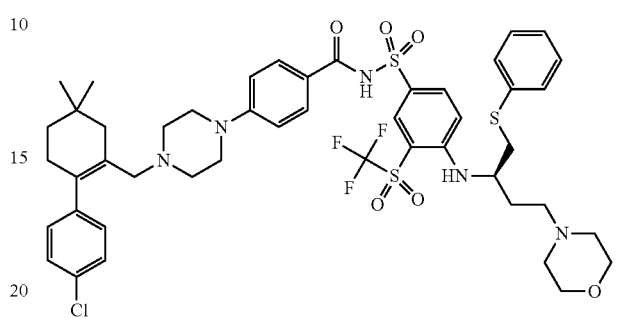

In another aspect, there are included compounds of formula (I), for use for inducing apoptose mediated by Mcl-1 protein.

A patient is effectively treated whenever a clinically beneficial result ensues. This may mean, for example, a complete resolution of the symptoms of a disease, a decrease in the severity of the symptoms of the disease, or a slowing of the disease's progression.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition.

Methods for Treating Cancers that are Responsive to the Modulation Mcl-1.

The present invention also relates to methods of administering the compositions to treat cancer, methods of killing cancer cells and methods of modulating levels of Mcl-1 in a cell. The therapeutic methods described herein can be carried out in connection with other cytotoxic therapies (e.g., chemotherapy, hormone therapy, radiotherapy, and antibody-based therapies).

In a preferred embodiment, the compound and the composition of the invention are useful for preventing or reducing metastasis or further dissemination in patient suffering from Mcl-1 expressing cancer more specifically, they are useful for increasing the duration of survival of such a patient, increasing the progression free survival of such a patient, increasing the duration of response, resulting in a statistically significant and clinically meaningful improvement of the treated patient as measured by the duration of survival, progression free survival, response rate or duration of response. In a preferred embodiment, the medicament is useful for increasing the response rate in a group of patients.

The details of one or more embodiments of the invention are set forth in the accompanying drawings and the description below. Other features, objects, and advantages of the invention will be apparent from the description and drawings, and from the claims.

DEFINITIONS

The following terms and expressions contained herein are defined as follows:

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, and alkoxycarbonyl, has the same meaning as alkyl defined above. Lower alkyl groups, which are preferred, are alkyl groups as defined above which contain 1 to 4 carbons. A designation such as "$C_1$-$C_6$ alkyl" refers to an alkyl radical containing from 1 to 6 carbon atoms.

As used herein, the term "alkenyl" refers to a straight chain, or branched hydrocarbon chains of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include ethenyl, propenyl, isopropenyl, 2,4-pentadienyl. "$C_2$-$C_4$ alkenyl" are particularly preferred.

As used herein, the term "alkoxy" means an alkyl-O— group wherein the alkyl group is as herein described. Exemplary alkoxy groups include methoxy, ethoxy, n-propoxy, i-propoxy, and n-butoxy.

As used herein, the term "aryl" refers to a substituted or unsubstituted, mono- or bicyclic hydrocarbon aromatic ring system having 6 to 10 ring carbon atoms. Examples include phenyl and naphthyl.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl.

As used herein, the term "arylalkenyl" refers to an alkenyl group that is substituted with an aryl group. Examples of arylalkenyl include, but are not limited to, styryl.

As used herein, the term "arylcarbonyl" refers to an aryl-C(=O)— group wherein the aryl group is as herein described.

As used herein, the term "arylalkylcarbonyl" refers to an arylalkyl-C(=O)— group wherein the arylalkyl group is as herein described.

As used herein, the term "heteroaryl" refers to an aromatic group containing 5 to 10 ring carbon atoms, preferably 5 to 7, in which one or more ring carbon atoms are replaced by at least one hetero atom such as —O—, —N—, or —S—. Examples of heteroaryl groups include pyrrolyl, furanyl, thienyl, pyrazolyl, imidazolyl, thiazolyl, isothiazolyl, isoxazolyl, oxazolyl, oxathiolyl), oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorders. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The meanings of all the other terms used in the description of the present invention are well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically acceptable salts, other salts are included in the invention. They may serve as intermediates in the purification of the compounds, in the preparation of other salts, or in the identification and characterization of the compounds or intermediates.

EXAMPLES

Figure 1A:
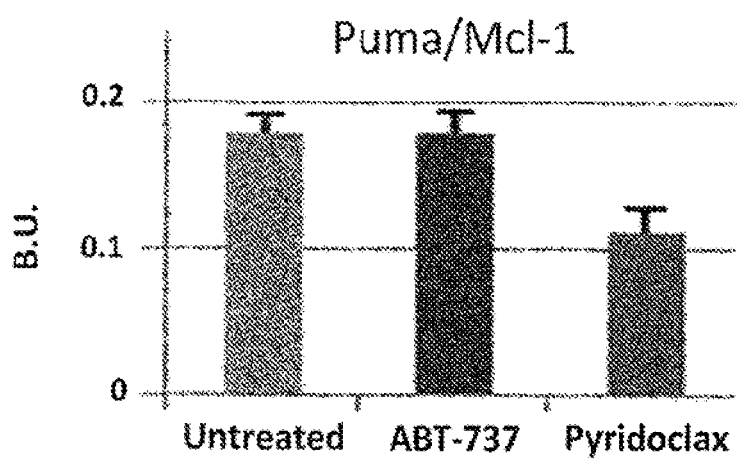
FIG. 1 shows the effect of Pyridoclax and ABT-737 on Mcl-1/Puma and Noxa/Mcl-1 interactions in BRET assay (FIGS. 1A and 1B, respectively); Pyridoclax is able to disrupt both Mcl-1/Puma and Noxa/Mcl-1 interactions whereas ABT-737 is not able to modify these interactions.

I. Synthesis of Compounds of Formula (I)

Material and method are described below.

Material

Commercial reagents were used as received without additional purification. Melting points were determined on a Kofler heating bench. IR spectra were recorded on a Perkin Elmer BX FT-IR spectrophotometer. The band positions are given in reciprocal centimeters (cm$^{-1}$). $^1$H NMR (400 MHz) and $^{13}$C NMR (100 MHz) spectra were recorded on a JEOL Lambda 400 spectrometer. Chemical shifts are expressed in parts per million downfield from tetramethylsilane as an internal standard and coupling constants in Hertz. Chemical shift are reported in part per million (ppm) relative to the solvent resonance. Chromatography was carried out on a column using flash silica gel 60 Merck (0.063-0.200 mm) as the stationary phase. The during solvent indicated for each purification was determined by thin layer chromatography (TLC) performed on 0.2 mm precoated plates of silica gel 60F-264 (Merck) and spots were visualized using an ultraviolet-light lamp. Elemental analyses for new compounds were performed and the data for C, H, and N were within ±0.4 of the theoretical values for all final compounds.

Methods (Het)aromatic oligosystems of the invention were synthesized according to the same procedure as that used to obtain MR29072 from 4-bromo-2-hydroxypyridine 1, trans-phenylvinylboronic acid 4 and 6-bromo-S-methylpyridin-3-ylboronic acid 7, and which is set out in scheme 1 and in example 1 below.

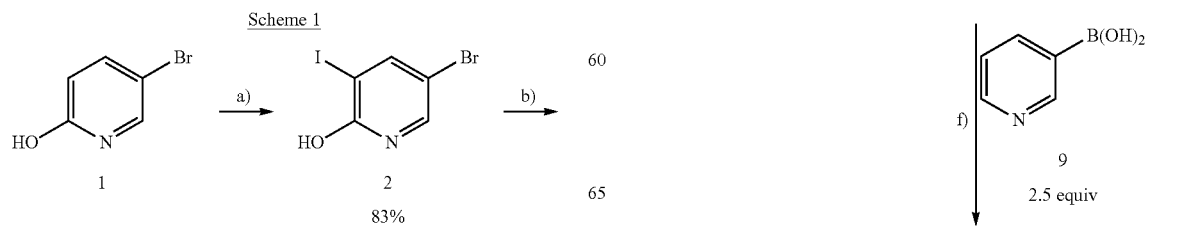

Scheme 1

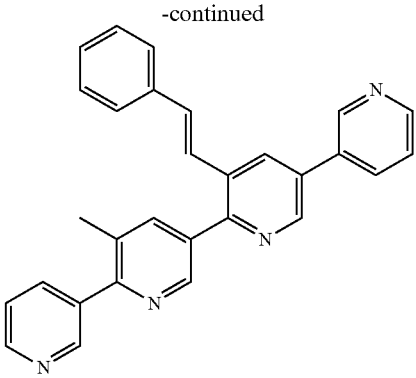

MR29072

86%

Conditions:
a) NIS (1.1 equiv), CH₃CN, rfx, 4 h;
b) PhPOCl₂, 160° C., 4 h;
c) Pd(PPh₃)₄ (0.05 equiv), Na₂CO₃ (2.5 equiv), 1,4-dioxane, rfx, 24 h;
d) NaI (5 equiv), CH₃COCl (1.5 equiv), CH₃CN, 100° C., 1 h, C = 0.25M, microwaves;
e) Pd(PPh₃)₄ (0.05 equiv), K₃PO₄ (2.5 equiv), DME, rfx, 20 h;
f) Pd(PPh₃)₄ (0.1 equiv), Na₂CO₃ (5 equiv). 1,4-dioxane, rfx, 24 h.

Example 1

5,6'-di(pyridin-3-yl)-5'-methyl-3-((E)-styryl)-2,3'-bipyridine (MR 29072)

To 5-bromo-2-hydroxypyridine 1 (5 g, 29 mmol) was added solid N-Iodosuocinimide (7.1 g, 32 mmol) in acetonitrile (120 mL). The solution was stirred at reflux fir 4 hours and followed by TLC. The solution was cooled to room temperature, filtered and washed with methanol, 5-bromo-2-hydroxy-3-iodopyridine 2 was obtained as a pink solid (yield: 83%).

2 (9 g, 30 mmol) was dissolved in phenylphosphonic dichloride 90% (100 mL, 0.3 mol). The mixture was stirred and heated (160° C.) for 4 hours and followed by TLC. At room temperature, it was introduced drops in a vial of 1 L filled with water and cooled at 0° C. The solution was neutralized by addition of NH₄OH solution. The mixture was extracted in ethyl acetate. The product was obtained as a white solid, 5-bromo-2-chloro-3-iodopyridine 3 (yield: 82%).

To a reaction vessel (100 mL) in a nitrogen environment containing 3 (5 g, 15.7 mmol) were added trans-phenylvinylboronic acid 4 (2.7 g, 18 mmol), tetrakis triphenylphosphine (907 mg, 0.8 mmol), sodium carbonate (4.2 g, 39 mmol) in 1,4-dioxane (100 mL). The mixture was stirred at reflux for 24 hours until consumption of starting material followed by TLC. The product was cooled to room temperature; it was filtered on celite. The solution was dried on MgSO₄, filtered and evaporated. The residue was purified by chromatography (c-hexane:ethyl acetate=99:1, then 98:2) to afford 5-bromo-2-chloro-3-((E)-styryl)-pyridine 5 (yield: 93%).

To 5 (200 mg, 0.7 mmol) were added sodium iodide (1 g, 6.8 mmol), acetyl chloride (0.07 mL, 1 mmol), and acetonitrile (10 mL). The solution was stirred under microwaves irradiation for 1 hour at 100° C. At room temperature, the mixture was neutralized by a NaHCO₃ solution. After an extraction and a wash with sodium bisulfite solid/water, the organic layer was dried with MgSO₄, filtered and evaporated. The product was purified by chromatography (c-hexane:ethyl acetate=98:2, then 95:5) to achieve at 5-bromo-2-iodo-3-((E)-styryl)-pyridine 6 (yield: 84%).

To a reaction vessel (100 mL) in a nitrogen atmosphere containing 6 (1.4 g, 3.6 mmol) were added 6-bromo-5-methylpyridin-3-ylboronic acid 7 (978 mg, 4.5 mmol), tetrakis triphenylphosphine (210 mg, 0.18 mmol), potassium phosphate (2.1 g, 9 mmol) in 1,2-dimethoxyethane (30 mL). The mixture was stirred at reflux for 20 hours until consumption of starting material followed by TLC. At room temperature, the solution was extracted with ethyl acetate. The organic layer was dried on MgSO₄, filtered and evaporated. The residue was purified by chromatography (c-hexane:ethyl acetate=95:5, then 9:1 and 8:2) and 5,6'-dibromo-5'-methy-3-((E)-styryl)-2,3'-bipyridine 8 (yield: 86%) was obtained.

To a reaction vessel (100 mL) in a nitrogen atmosphere containing 8 (320 mg, 0.7 mmol) were added pyridin-3-yl boronic acid 9 (156 mg, 1.7 mmol), tetrakis triphenylphosphine (78 mg, 0.07 mmol), sodium carbonate (355 mg, 3.35 mmol) in 1,4-dioxane (20 mL). The mixture was stirred at reflux for 24 hours until consumption of starting material followed by TLC. At room temperature, the suspension was filtered on celite and the solution was extracted with ethyl acetate. The organic layer was dried on MgSO₄, filtered and evaporated. The product was purified by chromatography (c-hexane:ethyl acetate=8:2, then 7:3 and 50:50) to achieve 5,6'-di(pyridin-3-yl)-5'-methyl-3-((E)-styryl)-2,3'-bipyridine MR29072 (yield: 86%) as a white solid (Mp 158° C.). IR (KBr): 2957, 1727, 1575, 1274, 1125, 1014, 967, 801, 770, 688 cm⁻¹. ¹H NMR (400 MHz, CDCl₃): δ 8.98 (d, ⁴J=1.9 Hz, 1H), 8.91 (d, ⁴J=1.9 Hz, 1H), 8.87 (m, 2H), 8.72 (dd, ³J=4.9 Hz, ⁴J=1.9 Hz, 2H), 8.68 (dd, ³J=4.9 Hz, ⁴J=1.9 Hz, 1H), 8.24 (d, ⁴J=1.9 Hz, 1H), 8.00 (m, 3H), 7.48 (d, ³J=7.8 Hz, 3H), 7.44 (dd, ³J=7.8 Hz, ⁴J=1.9 Hz, 1H), 7.36 (d, ³J=7.8 Hz, 1H), 7.31 (d, ³J=7.8 Hz, 1H), 7.28 (d, ³J=16.6 Hz, 1H), 7.23 (di, ³J=16.6 Hz, 1H), 2.51 (s, 3H). ¹³C NMR (100 MHz, CDCl₃): δ 155.3, 153.4, 149.9, 149.6, 149.2, 148.2, 148.0, 146.9, 139.8, 136.5, 136.3, 135.8, 134.4, 134.1, 133.1, 133.0, 132.9, 132.6, 132.0, 131.1, 128.8 (2C), 128.5, 126.8 (2C), 124.6, 123.8, 123.2, 20.0. LCMS (EI): m/z (%)=[M+H]⁺ theoretical: 427.53, experimental: 427.32. Anal. Calcd for C₂₉H₂₂N₄: C, 81.67; H, 5.20; N, 13.14. Found: C, 81.65; H, 5.25; N, 13.23.

This first procedure is applied to compounds 3-methyl-5-(3-(E)-styryl-5-(thiophen-3-yl)pyridin-2-yl)-2-(thiophen-3-yl)pyridine (MR31322), 3-methyl-2-(3-methylthiophen 2-yl)-5-(5-(3-methylthiophen-2-yl)-3-(E)-styrylpyridin-2-yl)pyridine (MR31336), 3-methyl-5-(3-(E)-styryl-5-(thiophen-2-yl)pyridin-2-yl)-2-(thiophen-2-yl)pyridine (MR31321), 2-(5-methyl-6-(1H-pyrazol-5-yl)pyridin-3-yl)-5-(1H-pyrazol-5-yl)-3-styrylpyridine (MR31363), 5-(2-chloro-1-methyl-1H-imidazol-5-yl)-2-(6-(2-chloro-1-methyl-1H-imidazol-5-yl)-5-methylpyridin-3-yl)-3-styrylpyridine (MR31351), 3-methyl-2-(4-cyanophenyl)-5-(5-(4-cyanophenyl)-3-styrylpyridin-2-yl)pyridine MR30854, 5-(3,4,5-trimethoxyphenyl)-2-(6-(3,4,5-trimethoxyphenyl)-5-methylpyridin-3-yl)-3-styrylpyridine (MR30847), 2-(3,4-dimethoxyphenyl)-5-(5-(3,4-dimethoxyphenyl)-3-styrylpyridin-2-yl)-3-methylpyridine (MR30846), 4-(3-methyl-5-(5-(pyridin-4-yl)-3-styrylpyridin-2-yl)pyridin-2-yl)pyridine (MR31350) 3-methyl-2-phenyl-5-(5-phenyl-3-styrylpyridin-2-yl)pyridine (MR30814), 5-(3-methyl-5-(5-(pyrimidin-5-yl)-3-styrylpyridin-2-yl)pyridin-2-yl)pyrimidine (MR31361)

From 5,6'-dibromo-5'-methyl-3-((E)-styryl)-2,3'-bipyridine 8 introduced in a reaction vessel (100 mL) in a nitrogen atmosphere with thiophene-3-boronic acid, 3-methyl-thiophene-2-boronic acid, thiophene-2-borinic acid, 1-(tetrahydro-2H-pyran-2-yl) 5-(4,4,5,5-tetramethyl-1,3,2-dioxoborolan-2-yl)-1H-pyrazole, 2-chloro-1-methyl-5-(4,4,5,5-tetramethyl-)-1,3,2-dioxaborolan-2-yl)-1H-imidazole, 4-cyano phenylboronic acid, 3,4,5-trimethoxyphenylboronic acid, 3,4-dimethoxyphenylboronic acid, 4-(4,4,5,5-tetramethyl-1,3,2-dioxaborolan-2-yl)pyridine, benzeneboronic acid, pyrimidin-5-yl boronic acid, tetrakis triphenylphosphine, sodium carbonate in 1,4-dioxane (20 mL), we respectively obtained MR31322, MR31336, MR31321. MR31363, MR31351, MR30854, MR30847, MR30846, MR31350, MR30814, MR31361.

Example 2

3-methyl-5-(3-(E)-styryl-5-(thiophen-2-yl)pyridin-2-yl)-2-(thiophen-2-yl)pyridine (MR31321)

$^1$H-NMR (CDCl$_3$) δ 8.90 (d, 1H, H6', J=1.96 Hz), 8.73 (d, 1H, H6, J=1.96 Hz), 8.18 (d, 1H, H4', J=1.96 Hz), 7.95 (d, 1H, H4, J=1.96 Hz), 7.58 (d, 1H, H3''', J=3.87 Hz), 7.49-7.46 (m, 4H, 2H ortho Ph, H5'' and H5'''), 7.43 (d, 1H, H3'', J=3.87 Hz), 7.38-7.34 (dd, 2H meta Ph, J=7 Hz), 7.30 (m, 1H para Ph, J=7 Hz), 7.20 (s, 2H, CH=CH), 7.19-7.17 (m, 2H, H4'' and H4'''), 2.68 (3H, CH$_3$).
MS(EI): 437[M+]*.

Example 3

3-methyl-5-(3-(E)-styryl-5-(thiophen-3-yl)pyridin-2-yl)-2-(thiophen-3-yl)pyridine (MR31322)

$^1$H-NMR (CDCl$_3$) δ 8.89 (d, 1H, H6, J=1.92 Hz), 8.77 (d, 1H, H6', J=1.92 Hz), 8.21 (d, 1H, H4, J=1.92 Hz), 7.96 (1H, H4', J=1.92 Hz), 7.68-7.66 (dd, 2H, H5'' and H5''', J=2.92 Hz, J=7.4 Hz), 7.57 (d, 1H, H para Ph, J=7 Hz) 7.51 (d, 2H, H2' and H5''', J=2.92 Hz), 7.47 (d, 2H ortho Ph, J=7 Hz), 7.43-7.41 (dd, 2H, H4'' and H4''', J=2.92 Hz), 7.38-7.34 (dd, 2H meta Ph, J=7 Hz), 7.26-7.21 (m, 2H, CH=CH), 2.68 (s, 3H, CH$_3$).
MS(EI): 437 [M+]*.

Example 4

3-methyl-2-(3-methylthiophen-2-yl)-5-(5-(3-methylthiophen-2-yl)-3-(E)-styrylpyridin-2-yl)pyridine (MR31336)

$^1$H-NMR (CDCl$_3$): 8.68 (d, 1H, H6, J=1.92 Hz), 8.59 (d, 1H, H6', J=1.92 Hz), 8.07 (d, 1H, H1, J=1.92 Hz), 7.95 (d, 1H, H4', J=1.92 Hz), 7.52-7.28 (m, 7H), 7.25-7.6.95 (m, 4H), 2.41 (s, 3H, CH$_3$), 2.16 (s, 3H, CH3), 2.03 (s, 3H, CH$_3$).
MS(EI): 466 [M++H, 100].

Example 5

2-(5-methyl-6-(1H-pyrazol-5-yl)pyridin-3-yl)-5-(1H-pyrazol-5-yl)-3-styrylpyridine (MR31363)

$^1$H-NMR (d$_6$-DMSO): δ 9.08 (d, 1H, J=1.7 Hz), 8.65 (d, 1H, J=1.7 Hz), 8.58 (d, 1H, J=1.7 Hz), 7.98 (d, 1H, J=1.6 Hz), 7.86 (d, 1H, J=1.5 Hz), 7.76 (bs, 1H), 7.55 (d, 2H, J=7.8 Hz), 7.45 (d, 1H, CH=CH, J=16.4 Hz), 7.40-7.36 (m, 2H), 7.31-7.27 (m, 1H), 7.22 (d, 1H, CH=CH, J=16.4 Hz), 7.02 (d, 1H, J=2.16), 6.86 (m, 1H), 6.53 (bs, 1H), 2.65 (s, 3H, CH$_3$).
MS(EI): 405.60 [M$^+$]*.

Example 6

5-(2-chloro-1-methyl-1H-imidazol-5-yl)-2-(6-(2-chloro-1-methyl-1H-imidazol-5-yl)-5-methylpyridin-3-yl)-3-styrylpyridine (MR31351)

$^1$H-NMR (CDCl$_3$): δ 8.82 (d, 1H, J=2.2 Hz), 8.66 (d, 1H, J=2.2 Hz), 8.04 (d, 1H, J=2.2 Hz), 7.99 (d, 1H, J=2.2 Hz), 7.39 (d, 2H, J=7.3 Hz), 7.32-7.25 (m, 3H), 7.18 (s, 1H), 7.14 (d, 1H, J=16 Hz), 7.12 (s, 1H), 7.10 (d, 1H, J=16 Hz), 3.69 (s, 3H, CH$_3$), 3.65 (s, 3H, CH$_3$), 2.47 (s, 3H, CH$_3$).
MS(EI): 501.13 [M$^+$]*, 503.12 [M$^+$+2]*, 505.32 [M$^+$+4]*.

Example 7

3-methyl-2-(4-cyanophenyl)-5-(5-(4-cyanophenyl)-3-styrylpyridin-2-yl)pyridine (MR30854)

$^1$H NMR (400 MHz, CDCl$_3$): δ 8.88 (d, J=2.2, 1H, H2'), 8.85 (d, J=2.2, 1H, H6), 8.24 (d, J=2.2, 1H, H4), 8.04 (d, J=2.2, 1H, H4'), 7.79 (dd, J=8.3, 1.9, 4H), 7.74 (dd, J=8.5, 2.0, 4H), 7.45 (d, J=8.0, 2H, Hstyr), 7.35 (d, J=8.1, 2H, Hstyr), 7.31 (d, J=7.3, 1H, Hstyr), 7.17 (d, J=16.3, 2H, CH=CH), 2.49 (s, 3H, CH$_3$).

Example 8

5-(3,4,5-trimethoxyphenyl)-2-(6-(3,4,5-trimethoxyphenyl)-5-methylpyridin-3-yl)-3-styrylpyridine (MR30847)

$^1$H NMR (400 MHz, CDCl$_3$): δ 8.83 (s, 1H, H6), 8.80 (s, 1H, H2'), 8.16 (s, 1H, H4), 7.99 (s, 1H, H4'), 7.49 (d, J=7.1, 2H, Hstyr), 7.35 (dd, J=7.6, 6.8, 2H, Hstyr), 7.31 (d, J=7.3, 1H, Hstyr), 7.28 (d, J=15.6, 1H, CH=CH), 7.21 (d, J=15.6, 1H, CH=CH), 6.86 (s, 2H), 6.84 (s, 2H), 3.99 (s, 6H, CH$_3$O-meta), 3.93 (s, 3H, CH$_3$O-para), 3.91 (s, 6H, CH$_3$O-meta'), 3.82 (s, 3H, CH$_3$O-para'), 2.50 (s, 3H, CH$_3$).

Example 9

2-(3,4-dimethoxyphenyl)-5-(5-(3,4-dimethoxyphenyl)-3-styrylpyridin-2-yl)-3-methylpyridine (MR301846)

$^1$H NMR (400 MHz, CDCl$_3$): δ 8.84 (s, 1H, H6), 8.80 (s, 1H, H2'), 8.17 (s, 1H, J=8.3, 1H, Hstyr), 7.28 (d, J=16.4, 1H, CH=CH), 7.27-7.21 (m, 4H), 7.18 (d, J=15.9, 1H, CH=CH), 7.04 (d, J=8.3, 1H), 6.98 (d, J=8.3, 1H), 4.01 (s, 3H, CH$_3$O-meta'), 3.97 (s, 9H), 2.50 (s, 3H, CH$_3$).

Example 10

4-(3-methyl-5-(5-(pyridin-4-yl)-3-styrylpyridin-2-yl)pyridin-2-yl)pyridine (MR31350)

$^1$H-NMR (CDCl$_3$): δ 8.85 (d, 1H, J=2.2 Hz), 8.80 (d, 1H, J=1.9 Hz), 8.73-8.71 (dd, 2H, J=1.7 Hz, J=4.5 Hz), 8.70-8.68 (dd, 2H, J=1.7 Hz, J=4.5 Hz), 8.21 (d, 1H, J=2.2 Hz), 7.97 (d, 1H, J=1.9 Hz), 7.58-7.57 (dd, 2H, J=1.7 Hz, J=4.5 Hz), 7.48-7.47 (dd, 2H, J=1.7 Hz, J=4.5 Hz), 7.41 (d, 2H, J=6.8 Hz), 7.32-7.29 (m, 2H), 7.26-7.25 (m, 1H), 7.23-7.16 (m, 2H, CH=CH), 2.43 (s, 3H, CH3).
MS (EI): 427.37 [M$^+$]*

Example 11

3-methyl-2-phenyl-5-(5-phenyl-3-styrylpyridin-2-yl)pyridine (MR30814)

$^{13}$C NMR (100 MHz, CDCl$_3$): δ 158.4, 153.1, 146.9, 146.2, 140.3, 139.7, 137.5, 136.8, 135.9, 133.3, 132.5 (2C), 131.7, 130.6, 129.3 (2C), 129.2 (2C), 128.8 (2C), 128.3 (2C), 128.2 (2C), 128.1, 127.2 (2C), 126.8 (2C), 125.4, 20.1. LCMS (ESI) (m/z): 424.55; [M+H$^+$] 425.27.

Example 12

5-(3-methyl-5-(5-(pyrimidin-5-yl)-3-styrylpyridin-2-yl)pyridin-2-yl)pyrimidine (MR31361)

$^1$H-NMR (CDCl$_3$): δ 9.33 (s, 1H), 9.30 (s, 1H), 9.10 (s, 2H), 9.07 (s, 2H), 8.90 (d, 1H, J=1.9 Hz), 8.88 (d, 1H J=2.2 Hz), 8.25 (d, 1H, J=2.2 Hz), 8.07 (d, 1H, J=1.9 Hz), 7.48 (d, 2H, J=7 Hz), 7.40-7.32 (m, 3H), 7.27 (d, 1H, J=16 Hz, CH=CH), 7.22 (d, 1H, J=16 Hz, CH=CH), 2.53 (s, 3H, CH$_3$).

MS(EI): 429.58 [M$^+$]*.

A second and a third procedure (Scheme 2) were applied to compounds 3-methyl-5-(5-phenyl-3-styrylpyridin-2-yl)-2-(pyridin-3-yl)pyridine (MR31348), 3-(6-(5-methyl-6-phenylpyridin-3-yl)-5-styrylpyridin-3-yl)pyridine (MR131349), 3-(3-methyl-5-(5-(pyridin-3-yl)-3-styrylpyridin-2-yl)pyridin-2-yl)phenol (MR31364), 3-(3 methyl-5-(5-(pyridin-3-yl)-3-styrylpyridin-2-yl)pyridin-2-yl)phenol (MR31366), (1Z)—N'-hydroxy-2-(3-(3-methyl-5-(5-(pyridin-3-yl)-3-styrylpyridin-2-yl)pyridin-2-yl)phenyl)acetamidine (MR31367), 5-(3,4-dimethoxyphenyl)-2-(6-(3,4,5-trimethoxyphenyl)-5-methylpyridin-3-yl)-3-styrylpyridine (MR30849), 5-(3,4,5-trimethoxyphenyl)-2-(6-(3,4-dimethoxyphenyl)-5-methylpyridin-3-yl)-3-styrylpyridine (MR30850).

Scheme 2

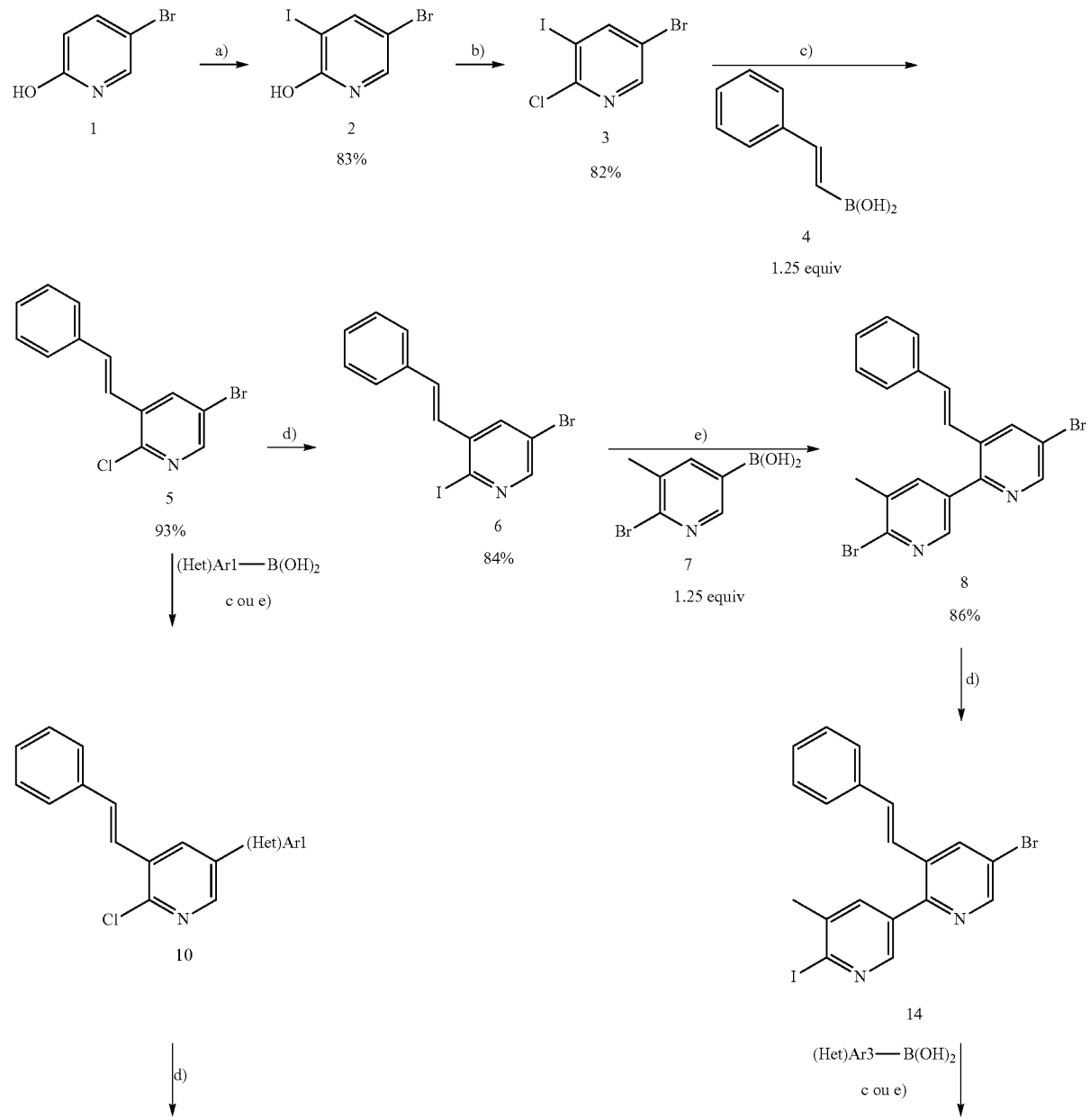

-continued
25
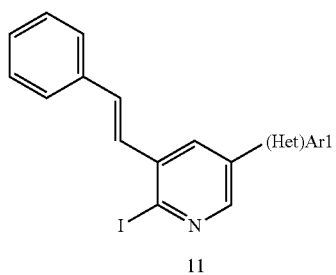
11
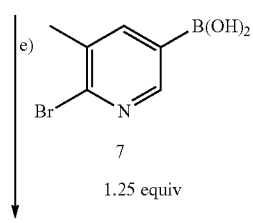
7
1.25 equiv
e)
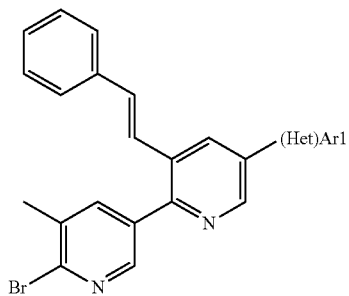
12
(Het)Ar2—B(OH)₂
c ou e)
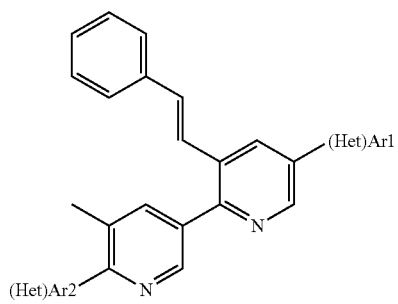
MR31348
MR31349
MR31364
MR31366
MR31367
26
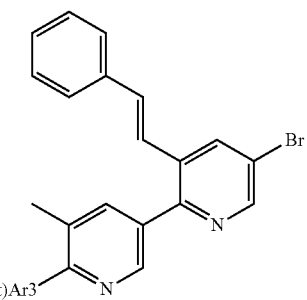
15
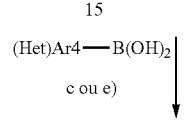
(Het)Ar4—B(OH)₂
c ou e)
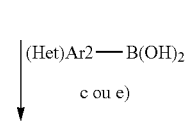
MR30849
MR30850
Conditions:
a) NIS (1.1 equiv), CH₃CN, rfx, 4 h;
b) PhPOCl₂, 160° C., 4 h;
c) Pd(PPh₃)₄ (0.05 equiv), Na₂CO₃ (2.5 equiv), 1,4-dioxane, rfx, 24 h;
d) NaI (5 equiv), CH₃COCl (1.5 equiv), CH₃CN, 100° C., 1 h, C = 0.25M, microwaves;
e) Pd(PPh₃)₄ (0.05 equiv), K₃PO₄ (2.5 equiv), DME, rfx, 20 h;
f) Pd(PPh₃)₄ (0.1 equiv), Na₂CO₃ (5 equiv). 1,4-dioxane, rfx, 24 h.

Example 13

5-(3,4,5-trimethoxyphenyl)-2-(6-(3,4-dimethoxyphenyl)-5-methylpyridin-3-yl)-3-styrylpyridine (MR30650)

$^1$H NMR (400 MHz, CDCl$_3$): δ 8.83 (d, J=2.2, 1H, H6), 8.80 (d, J=2.2, 1H, H2'), 8.16 (d, J=2.4, 1H, H4), 7.98 (d, J=1.7, 1H, H4'), 7.49 (d, J=7.1, 2H, Ha), 7.36 (dd, J=7.6, 7.1, 2H, Hb), 7.30 (d, J=6.8, 1H, Hc), 7.21 (d, J=17.8, 1H, CH=CH), 7.20 (d, J=17.8, 1H, CH=CH), 7.20 (d, J=8.3, 1H), 7.19 (di, J=8.0, 1H), 6.98 (d, J=8.3, 1H), 6.86 (s, 2H), 3.99 (s, 6H), 3.97 (s, 3H), 3.96 (s, 3H), 3.94 (s, 3H), 2.50 (s, 3H, CH$_3$).

Example 14

5-(3,4-dimethoxyphenyl)-2-(6-(3,4,5-trimethoxyphenyl)-5-methylpyridin-3-yl)-3-styrylpyridine (MR30649)

$^1$H NMR (400 MHz, CDCl$_3$): δ 8.84 (d, J=2.2, 1H, H6), 8.79 (d, J=2.2, 1H, H2'), 8.17 (d, J=2.2, 1H, H4), 7.99 (d, J=2.0, 1H, H4'), 7.48 (d, J=7.3, 2H, Hstyr), 7.35 (dd, J=7.8, 6.8, 2H, Hstyr), 7.30 (d, J=7.1, 1H, Hstyr), 7.27 (d, J=2.2, 1H), 7.27 (d, J=16, 1H, CH=CH), 7.23 (d, J=16.2, 1H, CH=CH), 7.19 (d, J=2.2, 1H), 6.84 (s, 3H), 4.01 (s, 3H), 3.97 (s, 3H), 3.93 (s, 6H), 3.91 (s, 3H), 2.50 (s, 3H, CH$_3$).

Example 15

(1Z)—N'-hydroxy-2-(3-(3-methyl-5-(5-(pyridin-3-yl)-3-styrylpyridin-2-yl)pyridin-2-yl)phenyl)acetamidine (MR31367)

$^1$H-NMR (CDCl$_3$): δ 8.98 (d, 1H, J=1.96 Hz), 8.87 (d, 1H, J=2.2 Hz), 8.82 (d, 1H, J=2.2 Hz), 8.72 (d, 1H, J=1.96 Hz), 8.24 (d, 1H, J=2.2 Hz), 8.02-8.00 (m, 2H), 7.55-7.43 (m, 7H), 7.36-7.20 (m, 4H), 4.58 (bs, 1H, NH$_2$), 3.56 (s, 2H, CH$_2$), 2.46 (s, 3H, CH$_3$).

MS(EI): 498.55 [M$^+$]*

Example 16

3-(3-methyl-5-(5-(pyridin-3-yl)-3-styrylpyridin-2-yl)pyridin-2-yl)phenol (MR31366)

$^1$H-NMR (CD$_3$OD): δ 10.5 (bs, 1H, COOH), 9.02 (d, 1H, J=1.96 Hz), 8.90 (d, 1H, J=2.2 Hz), 8.68 (d, 1H, J=2.2 Hz), 8.66-8.64 (dd, 1H, J=1.2 Hz, J=4.6 Hz), 8.56 (d, 1H, J=2.2 Hz), 8.33-8.31 (dd, 1H, J=1.3 Hz, J=4.6 Hz), 8.07 (d, 1H, J=2.2 Hz), 7.63-7.62 (m, 1H), 7.53-7.48 (m, 5H), 7.37-7.33 (m, 2H), 7.29-7.21 (m, 2H), 3.71 (s, 2H, CH$_2$), 2.44 (s, 3H, CH$_3$)

MS(EI): 484.54 [M$^+$]*

Example 17

3-(3-methyl-5-(5-(pyridin-3-yl)-3-styrylpyridin-2-yl)pyridin-2-yl)phenol (MR31364)

$^1$H-NMR (CDCl$_3$): δ 8.98 (d, 1H, J=1.96 Hz), 8.86 (d, 1H, J=1.96 Hz), 8.78 (d, 1H, J=1.96 Hz), 8.72-8.71 (m, 1H) 8.26 (d, 1H, J=2.2 Hz), 8.03-7.99 (m, 3H), 7.51-7.46 (m, 3H), 7.35-7.32 (m, 2H), 7.31-7.20 (m, 4H), 7.07 (d, 1H, J=7.56 Hz), 6.93 (s, 1H), 6-84-6.81 (dd, 1H, J=1.6 Hz, J=7.56 Hz), 2.45 (s, 3H), 1.77 (bs, 1H, OH)

MS(EI): 442.41 [M$^+$]*

Example 18

3-(6-(5-methyl-6-phenylpyridin-3-yl)-5-styrylpyridin-3-yl)pyridine (MR31349)

$^1$H-NMR (CDCl$_3$): δ 8.90 (d, 1H, J=1.9 Hz), 8.79 (d, 1H, J=2.2 Hz), 8.75 (d, 1H, J=2.2 Hz), 8.64-8.62 (dd, 1H, J=1.2 Hz, J=4.7 Hz), 8.15 (d, 1H, J=2.2 Hz), 7.94-7.91 (m, 2H), 7.55 (d, 2H, J=7 Hz), 7.44-7.33 (m, 6H), 7.29-7.26 (m, 2H), 7.23-7.19 (m, 2H), 7.14 (d, 1H, J=16 Hz, CH=CH), 2.42 (s, 3H, CH3).

MS(EI): 426.42 [M$^+$]*

Example 19

3-methyl-5-(5-phenyl-3-styrylpyridin-2-yl)-2-(pyridin-3-yl)pyridine (MR31348)

$^1$H-NMR (CDCl$_3$): δ 8.90 (d, 1H, J=1.9 Hz), 8.88 (d, 1H, J=2.2 Hz), 8.86 (d, 1H, J=1.9 Hz), 8.68-8.67 (dd, 1H, J=1.7 Hz, J=4.8 Hz), 8.24 (d, 1H, J=1.9 Hz), 8.03 (d, 1H, J=1.7 Hz), 7.98-7.97 (m, 1H), 7.72 (d, 2H, J=8.3 Hz), 7.57-7.53 (m, 2H), 7.49-7.46 (m, 4H), 7.38-7.34 (m, 2H), 7.31-7.29 (m, 1H), 7.27 (d, 1H, J=16.6 Hz), 7.22 (d, 1H, J=16.6 Hz), 2.50 (s, 3H, CH3).

MS(EI): 426.58 [M$^+$]*

II. Biological Activity of Compounds of Formula (I)

II.A. Materials & Methods

Tested Compounds (Het)aromatic oligosystems are synthesized as described in Example 1 and purified by chromatography (column using flash silica gel 60 Merck [0.063-0.200 mm] as the stationary phase).

ABT-737 was obtained from Selleckchem (Houston, Tex., USA) and dimethylsulfoxide (DMSO) from Sigma-Aldrich (Saint-Quentin Fallavier, France).

These compounds were commonly stored as stock solutions in DMSO at −20° C.

Cell Culture

Human ovarian carcinoma OAW42 cell line was established from a human ovarian adenocarcinoma and was obtained from ECACC (Sigma-Aldrich, Saint Quentin Fallavier, France). It was grown in DMEM medium supplemented with 4500 mg/l glucose, 2 mM Glutamax, 1 mM sodium pyruvate, 10% fetal calf serum, 33 mM sodium bicarbonate (Gibco BRL, Lyon, France) and 20 IU/l recombinant human insulin (Lilly, Suresnes, France).

Human ovarian carcinoma SKOV3 cell line was established from a human ovarian adenocarcinoma and was obtained from American Type Culture Collection (Manassas, Va., USA), as well as the human malignant mesothelioma cell line NCI-H28 and the human lung carcinoma cell line A549.

IGROV1 cell line was kindly provided by Dr. J. Bénard (Institut G. Roussy, Villejuif, France). These cell lines were grown in RPMI 1640 medium supplemented with 2 mM Glutamax™, 25 mM HEPES, 10% fetal calf serum, and 33 mM sodium bicarbonate (Fisher Scientific, Illkirch, France), In vitro chemoresistant model of IGROV1 (IGROV1-R10) and OVW42 (OAW42-R) cell lines were obtained previously by mimicking a clinical protocol of cisplatin administration [Poulain et al. (1998) *Int J Cancer* 78, 454-463; Villedieu et al., (2007) Gynecol Oncol. 10(1), 31-44].

Cells were maintained at 37° C. in a 5% $CO_2$ humidified atmosphere and split twice a week by trypsinization.

Treatments

Exponentially growing cells were transfected by siRNA as described below, and after 48 h, cells were continuously exposed to (Het)aromatic oligosystems (10, 25 or 50 µM) dissolved in DMSO (<0.1% of total volume) for 4 to 24 supplementary hours.

Gene Silencing siRNAs were synthesized and annealed by Eurogentec (Liege, Belgium). Sequences were as follows:

Bcl-$x_L$ siRNA antisense (siXL1): 5'-auuggugagucggaucg-catt-3' (SEQ. ID. No1);

Mcl-1 siRNA (siMCL1): 5'-gugccuuuguggcuaacatt-3' (SEQ. ID. No2):

Control siRNA (siCONT): 5'-gacguaaacggccacaagutt-3' (SEQ. ID. No3).

The control siRNA does not bear any homology with any relevant human genes. Cells were seeded in 25 cm² flasks the day before to reach 30-50% confluency at the time of transfection. The transfection INTERFERin™ reagent (Polyplus Transfection, Strasbourg. France) was added to siRNA diluted in Opti-MEM® reduced serum medium (Invitrogen, Cergy-Pontoise, France) and complexes formation was allowed to proceed for 15 min at RT before being applied to cells. The final siRNA concentration in the flasks was 20 nM.

BRET Assay

Hela cells were seeded on 6-well plates and transfected with 200 ng/well of plasmid pRLuc-Bax, pRLuc-Puma or pRLuc-Noxa coding for BRET donors and 1 g/well of peYFP-Bcl-$x_L$ or peYFP-Mcl-1 coding for BRET acceptors (or with pCMV-Bcl-$x_L$ or pCMV-Mcl-1 for control). Twenty-four hours after transfection, cells were trypsinized and re-seeded into white 96 well plate flat bottom, incubated for another day, and then treated with drugs for 16 hours at 10 µM. Light emission at 485 nm and 530 nm was measured consecutively using the Mithras fluorescence-luminescence detector LB 940 (Berthold) after adding the luciferase substrate, coelenterazine H (Uptima) at a final concentration of 5 µM. BRET ratios were calculated as described [Terrillon et al. (2003) *Mol Endocrinol* 17, 677-691, Vo et al. (2012) Eur J Med Chem., 286-93].

Real-Time Cellular Activity Assay

Compound-mediated cytotoxicity was monitored using Real-Time Cell Analyzer multi-plate (RTCA MP) Instrument, xCELLigence System (Roche Applied Science, Mannheim, Germany). This system monitors cellular events in real time measuring electrical impedance across interdigitated micro-electrodes integrated on the bottom of tissue culture E-plates View (Roche). The increase in the number and size of cells attached to the electrode sensors leads to increased impedance, from which derive the Cell Index values (CI) displayed at the plot. Thus, this index reflects changes in cell viability as described by Ke et al. (2011, *Methods Mol Biol* 740, 33-43). Briefly, 96-well E-Plate were seeded with 3×10³ cells/well and placed onto the RTCA MP located inside a tissue culture incubator, where cells were left to grow for 24 h before treatment. Impedance was continuously measured until the end of the treatment. Standard deviations of well replicates were analyzed with the RTCA Software.

Apoptosis Assays

Morphological Characterization of Apoptotic Cells by Nuclear Staining with DAPI

After treatment, both detached and adherent cells were pooled after trypsinization, applied to a polylysine-coated glass slide by cytocentrifugation and fixed with a solution of ethanol/chloroform/acetic acid (6:3:1). The preparations were then incubated for 15 min at room temperature with 1 µg/ml DAPI solution (Boehringer Mannheim-Roche, Mannheim, Germany), washed in distilled water, mounted under a coverslip in Mowiol (Calbiochem) and analyzed under a fluorescence microscope (BX51, Olympus, Rungis, France).

Cell Cycle Analysis by Flow Cytometry

Adherent and floating cells were pooled, washed with 1×PBS and centrifuged at 200 g for 5 min before staining by Annexin V, propidium iodide or both, as recommended by the manufacturer (Roche Diagnostic, Indianapolis, USA). Briefly, 100 µl of Annexin V—Flit or propidium iodide or both were added on the cells pellet (10⁶ cells) and incubated 15 minutes at room temperature in obscurity. 500 µl of sample buffer was then added on the suspensions that were thereafter analyzed using a Gallios flow cytometer (Beckman Coulter, Roissy, France) and cell cycle distribution was determined using Kaluza acquisition software (Beckman Coulter).

Preparation of Cell Extracts and Western Blot Analysis

Cells were rinsed with ice-cold PBS, suspended in a lysis buffer [RIPA:NaCl 150 mM, Tris (pH 8) 50 mM, Triton X100 1%, PMSF 4 mM, EDTA 5 mM, NaF 10 mM, NaPPi 10 mM, Na3OV4 1 mM, aprotinin 0.5 µl/ml and 4.6 ml ultra pure water] and incubated on ice for 30 minutes. Lysates were collected after centrifugation (13200 g, 10 min, 4° C.) and protein concentrations were determined using the Bradford assay (Bio-Rad, Hercules, USA). 20 µg of protein were separated by SDS-PAGE on a 4-12% gradient polyacrylamide gel (Invitrogen, Cergy-Pontoise, France) and transferred to Hybond-PVDF membranes (Amersham, Orsay, France). After blocking non-specific binding sites for 1 hour at RT by 5% (w/v) non-fat dry milk in TBS with 0.1% (v/v) Tween20 (T-TBS), the membranes were incubated overnight at 4° C. with the following rabbit monoclonal antibody: PARP, caspase-3 and Bcl-$x_L$, Bim (Cell Signaling Technology, Ozyme, Saint-Quentin-en-Yvelines, France), Mcl-1 (Santa Cruz, Le Perray-en-Yvelines, France), HSP-70, Noxa (Calbiochem, Fontenay-sous-Bois, France), (Cell Signalling) and Actin (Sigma-Aldrich, Saint-Quentin Fallavier, France). Membranes were then washed with T-TBS and incubated for 1 hour with the appropriate horseradish peroxidase-conjugated anti-rabbit or anti-mouse (Amersham, Orsay, France) secondary antibodies. Revelation was done using a luminescent Image Analyzer (GE Healthcare, Orsay, France).

Transmission Electron Microscopy

Cells were fixed with 2.5% glutaraldehyde in PBS buffer, included in agar, rinsed in Sorensen's buffer, post-fixed in osmium tetroxide 1% in Sorensen's buffer, deshydrated in ethanol and embedded in EPON resin. Ultrathin sections were cut and stained with uranyl acetate and lead citrate and examined using a JEOL1011 transmission electron microscope.

II.B. RESULTS

II.B.1. Activity of Pyridoclax (MR29072)

Pyridoclax Disrupts Mcl-1/Puma Interaction

Figure 1B:
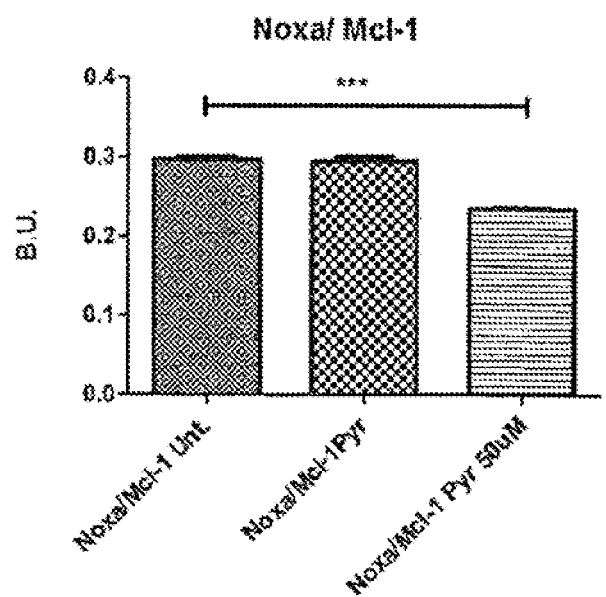

As presented on the FIGS. 1A and 1B, Pyridoclax is able to disrupt both Mcl-1/Puma and Mcl-1/Noxa interactions in a cellular assay (BRET) performed in Hela cells. Whereas ABT-737 is not able to modify this interaction, Pyridoclax induced a drastic inhibition of Mcl-1/Puma interaction (about 50%).

Effect of Pyridoclax as Single Agent or Associated to siRNA-Mediated Bcl-$x_L$ Inhibition To demonstrate the interest of Pyridoclax as a Mcl-1 inhibitor, a model of selective addiction to both Bcl-$x_L$ and Mcl-1 in which Bcl-$x_L$ expression is silenced by RNA interference 48 h before exposure has been used. The ovarian carcinoma cell line IGROV1-R10 is chosen to conduct these assays since it has been previously demonstrated that this cell line was highly sensitive to the concomitant inhibition of Bcl-$x_L$ and Mcl-1 (Brotin et al. (2010) Int J Cancer 126, 885-895), but remained viable when only one of these targets was inhibited.

As expected, neither Pyridoclax nor the Bcl-$x_L$ targeting siRNA (siXL1) induced massive cell death on their own. A slowed down proliferation is observed, but neither cell detachment, nor strong sub-G1 peak, caspase 3 activation and condensed or fragmented nuclei were observed (FIGS. 2A, B, C) in these conditions.

Figure 2:
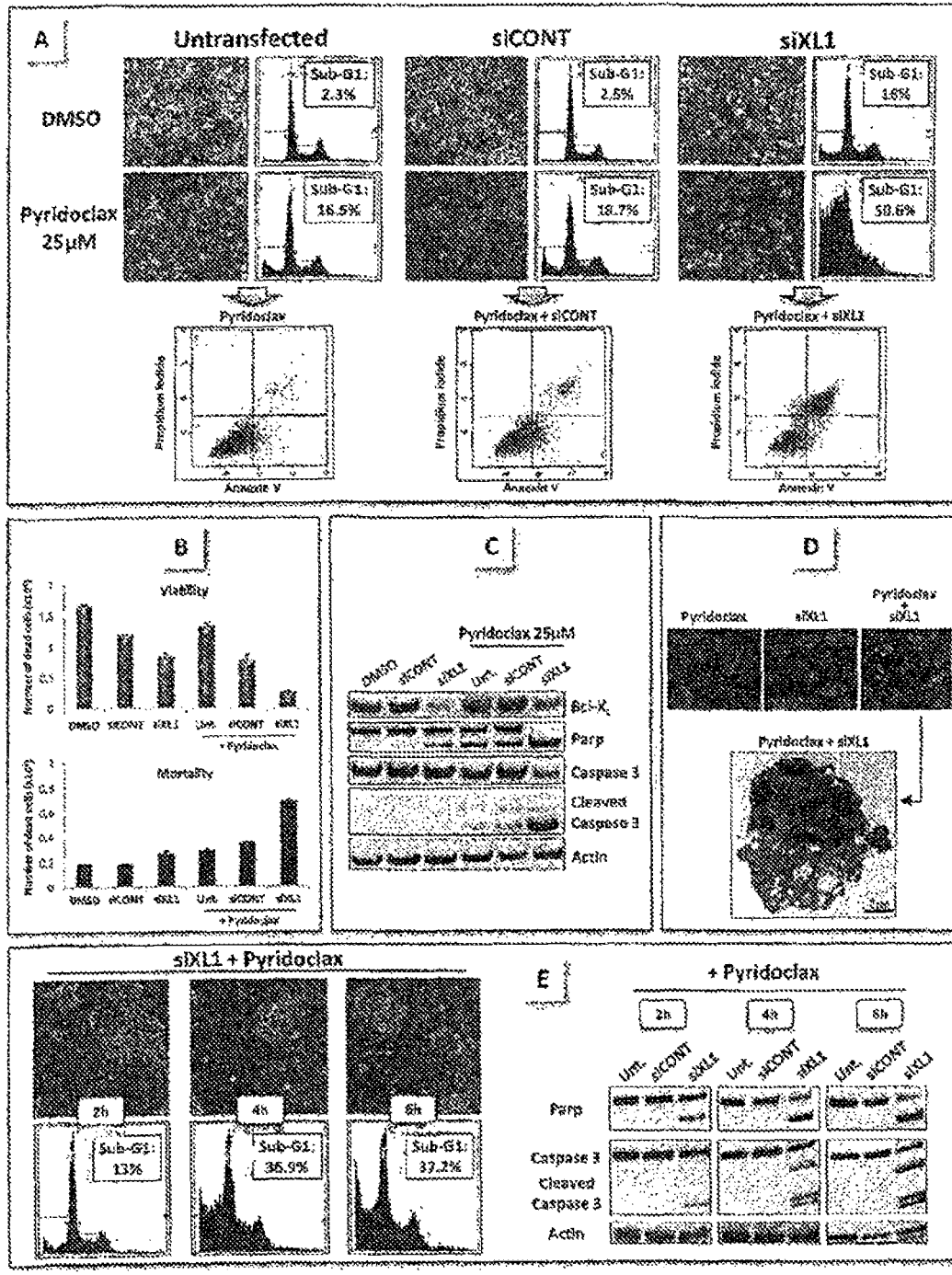
FIG. 2 shows the effect of Pyridoclax on IGROV1-R10 ovarian cancer cells, alone or associated to a Bcl-$x_L$ targeting siRNA (siXL1). Cells were transfected with 10 nM siRNA for 48 h before a 24 h (A, B, C, D) or 2, 4, 6 h (B) exposure to 25 μM Pyridoclax. [A] Cellular morphology, DNA content histograms and Annexin V/propidium iodide bi-parametric histograms. [B]: Trypan blue exclusion assay. [C]: Bcl-$x_L$ expression and PARP and caspase 3 cleavage assessed by western blot. [D]: Nuclear morphology studied after DAPI staining (top) and cellular morphology studied by electron microscopy. [E]: Short time effects of the association Pyridoclax/siXL1 (assessed 2, 4 and 6 h after the beginning of the exposure to Pyridoclax). Cellular morphology and DNA content histograms (left panel) and PARP and caspase 3 cleavage assessed by western blot (right panel).

In contrast, their association led to a massive cell death, as demonstrated by a strong cell detachment, by the appearance of a strong sub-G1 Peak on the DNA content histogram (over 50%) and of a 60% fraction of annexin V positive cells (FIG. 2A). Moreover, the viability evaluation showed that this association led to a drastic decrease of the number of viable cells and to a concomitant increase of dead cells (FIG. 2B) and western blot showed a complete cleavage of PARP and caspase 3. DAPI staining and electron microscopy showed that this association led to nuclear condensations and fragmentations (only when the two agent were combined), highly evocative of apoptotic cell death (FIG. 2D).

These effects are optimal after exposure to a concentration of 25 μM of Pyridoclax, but are also observed in a lower extend in response to 10 μM (data not shown).

The kinetic study of the effect of this combination showed that apoptosis was observed as soon as 2 to 4 h after the beginning of the exposure (37% of events in sub-G1 fraction after 4 h), this observation being compatible with a pharmacologic Mcl-1 inhibition through BH3-mimetic activity (FIG. 2E).

Altogether, these elements show that Pyridoclax strongly sensitizes ovarian cancer chemoresistant IGROV1-R10 cells to Bcl-$x_L$ targeting siRNA, their combination leading to massive apoptosis.

Pyridoclax Sensitizes Various Cancer Cell Types to Bcl-$x_L$ Targeting siRNA

Figure 3:
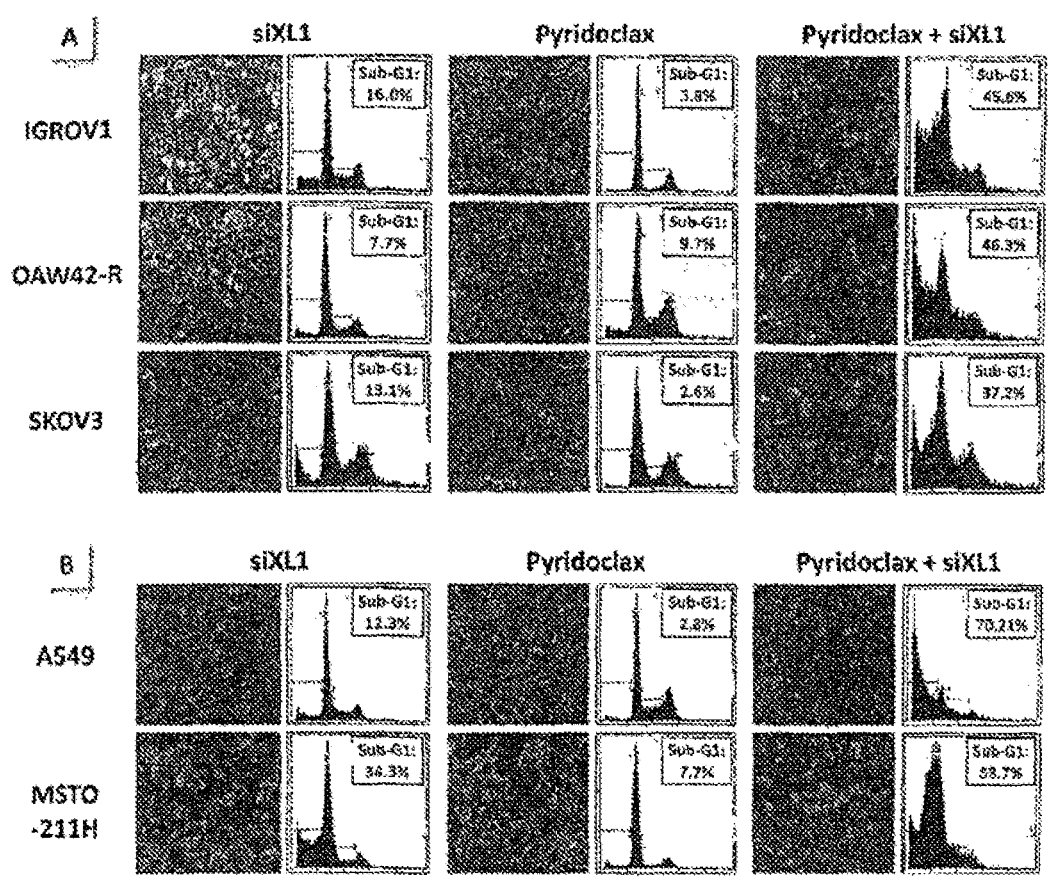
FIG. 3 illustrates the effect of Pyridoclax alone or associated to a Bcl-$x_L$ targeting siRNA (siXL1) on ovarian, lung and mesothelial cancer cell lines. Cells were transfected with 10 nM siRNA for 48 h before a 24 h exposure to 25 µM Pyridoclax. Cell detachment and sub-G1 fraction proportion on DNA histograms were assessed by the observation of cellular morphology and by flow cytometry, respectively, in ovarian carcinoma cells [A] and lung or mesothelioma cancer cells [B].

The effect of the combination of Pyridoclax with siXL1 in other ovarian carcinoma cell lines (FIG. 3A) as well as in other cancer cell types (FIG. 3B) has then been studied.

A similar response to this association is observed in all ovarian carcinoma cell lines, as well as in lung carcinoma (A549) and mesothelioma (NCI-H28 and MSTO-211H) cell lines.

Pyridoclax Sensitizes Chemoresistant Ovarian Cancer Cells to ABT-737

Figure 4:
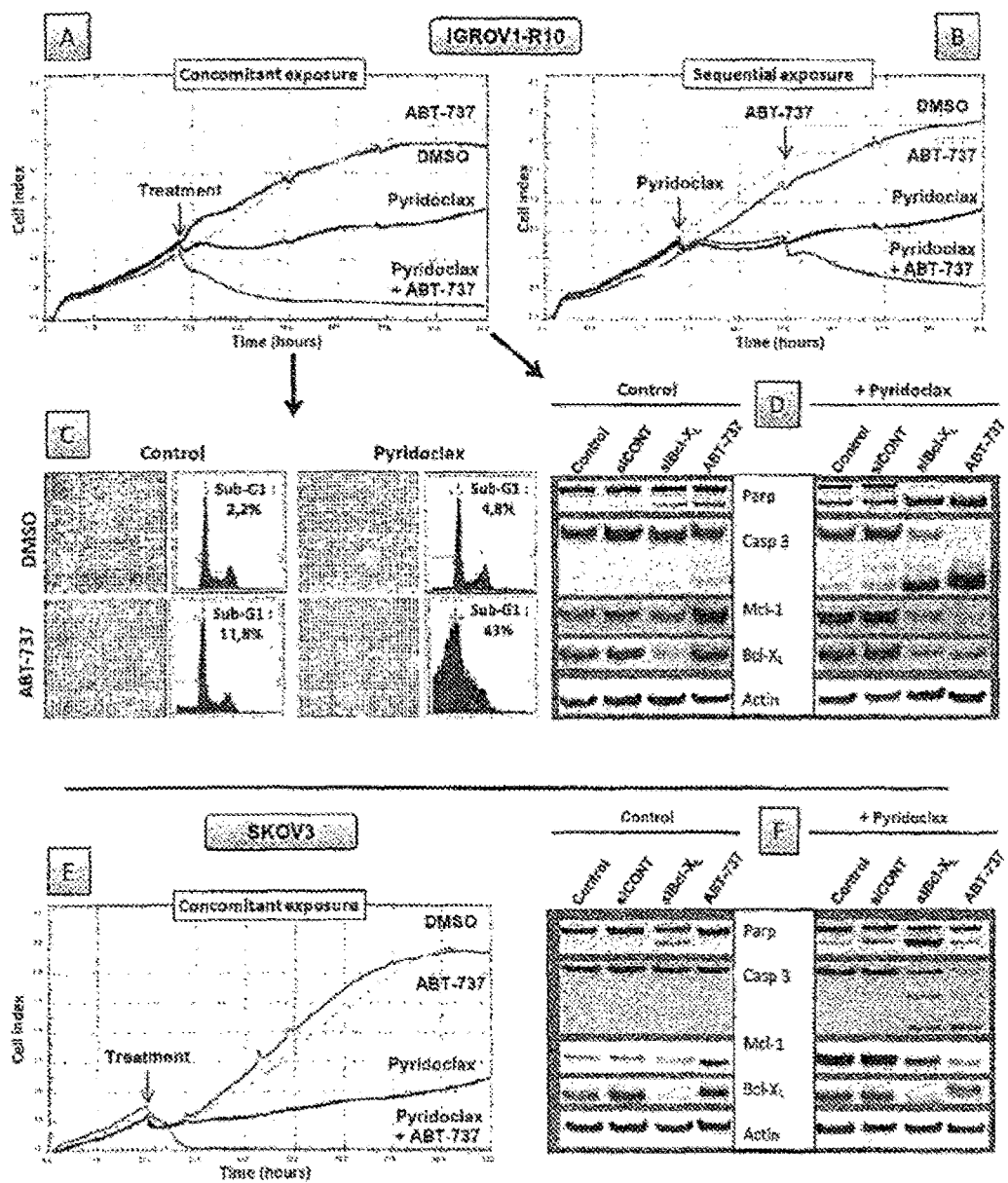
FIG. 4 represents the effect of the association of Pyridoclax with ABT-737 on chemoresistant ovarian cancer cells IGROV1-R10 (top) and SKOV3 (bottom). Cells were concomitantly (A, E) or sequentially (B) exposed to 25 µM Pyridoclax and 5 µM ABT-737, and cellular effects were assessed either longitudinally (A, B, E) or after 24 h (C, D, F). [A, B, E] real time cellular activity assessed by impedancmetry (xCELLigence technology), after concomitant exposure (A, E) or sequential exposure (B; 24 h Pyridoclax, then ABT-737). [C]: Cellular morphology and DNA content histograms after a 24 h concomitant exposure. [D and F]: PARP and caspase 3 cleavage after a 24 h concomitant exposure.

ABT-737 being yet one of the most potent Bcl-$x_L$ inhibiting BH3-mimetic molecule, and the response to ovarian cancer cells being conditioned by the inhibition of Mcl-1, the effect of the combination of ABT-737 with Pyridoclax has been evaluated (FIG. 4). As described previously with siXL1, it is observed that neither ABT-737 nor Pyridoclax induced cell death as single agents, whereas their combination led to massive apoptotic cell death in both IGROV1-R10 and SKOV3 chemoresistant ovarian cancer cell lines. Indeed, when the two molecules were combined, cellular activity was drastically decreased in both cell lines as assessed by impedancemetry (xCELLigence technology) (FIGS. 4A and 4D); furthermore a strong cell detachment and an important sub-G1 fraction are observed (FIG. 4B) as well as complete PARP and caspase 3 cleavages (FIGS. 4C and 4D right panel). It should be noticed that these effects were similar in concomitant exposure experiments and in sequential exposure (Pyridoclax 24 h, then ABT-737). Moreover, the observed apoptosis was quasi-immediate as soon as the cells are exposed to Pyridoclax and ABT-737, arguing in favor of a BH3-mimetic activity.

ILB.2. Activity of Other Compounds of the Invention

Compounds selected on their capability to disrupt the Mcl-1/Puma interaction in BRET assay have then been tested to assess their activity on cell morphology, on cell cycle, on PARP cleavage and on nuclear morphology; results are presented in Table I below:

TABLE I

| Molecule identification | | Molecule + Bcl-xL targeting siRNA | | | |
| --- | --- | --- | --- | --- | --- |
| | | Cell detachment | Sub-G1 (%) | PARP cleavage | Apoptotic nuclear features |
| 29072 or Pyridoclax | 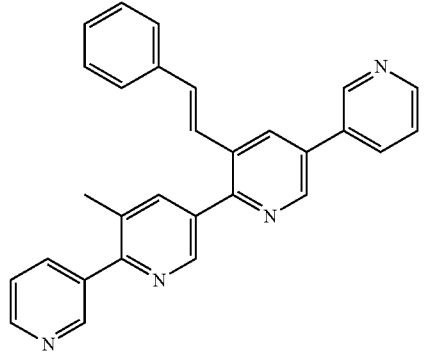 [SMILES: Cc1cc(-c2ncc(-c3cccnc3)cc2/C=C/c2ccccc2)cnc1-c1cccnc1] | +++ | 53.6 | +++ | +++ |

TABLE I-continued

| | | Molecule + Bcl-xL targeting siRNA | | | |
|---|---|---|---|---|---|
| Molecule identification | | Cell detachment | Sub-G1 (%) | PARP cleavage | Apoptotic nuclear features |
| 30814 | | − | 37.2 | + | + |
| 31349 | | ++ | 59.2 | +++ | +++ |
| 31348 | | +++ | 58.8 | +++ | +++ |
| 30846 | | − | 33.1 | nd | + |

TABLE I-continued

| Molecule identification | | Molecule + Bcl-xL targeting siRNA | | | |
|---|---|---|---|---|---|
| | | Cell detachment | Sub-G1 (%) | PARP cleavage | Apoptotic nuclear features |
| 30847 | [structure] | ± | 22 | nd | + |
| 30854 | [structure] | ± | 24.3 | nd | + |
| 31336 | [structure] | ++ | 48.8 | nd | ++ |
| 31351 | [structure] | +++ | 56.7 | nd | +++ |

TABLE I-continued

| Molecule identification | | Molecule + Bcl-xL targeting siRNA | | | |
|---|---|---|---|---|---|
| | | Cell detachment | Sub-G1 (%) | PARP cleavage | Apoptotic nuclear features |
| 31361 | (structure) | ++ | 35.2 | nd | ++ |
| 31363 | (structure) | +++ | 63.7 | nd | +++ |
| 30849 | (structure) | − | 19.9 | nd | + |
| 30850 | (structure) | − | 20.2 | nd | + |

TABLE I-continued

| Molecule identification | | Molecule + Bcl-xL targeting siRNA | | | |
|---|---|---|---|---|---|
| | | Cell detachment | Sub-G1 (%) | PARP cleavage | Apoptotic nuclear features |
| 30820 | (structure) | ++ | 57.8 | + | ++ |
| 31364 | (structure) | ++ | 39.6 | nd | ++ |
| 31366 | (structure) | +++ | 51 | nd | ++ |

TABLE I-continued

| Molecule identification | | Molecule + Bcl-xL targeting siRNA | | | |
|---|---|---|---|---|---|
| | | Cell detachment | Sub-G1 (%) | PARP cleavage | Apoptotic nuclear features |
| 31367 | (structure) | +++ | 52.7 | nd | +++ |

Assessment of the Different Criteria:

Cell Detachment:

"−" means no difference between untreated cells and those treated with the tested compound;

"±" means that very few cells were detached from the support (less than 10%);

"+" means that about 20% of cells were detached from the support;

"++" means that about half of the cells were detached from the support;

"+++" means that majority of the cells are detached from the support.

PARP Cleavage:

"+" means that a little band corresponding to the 85 kDa cleaved form of PARP is observable on the western blot. This band is usually absent or weak when cells are untreated, the only band observable being thus the 110 kDa band;

"++" means that a band corresponding to the 85 kDa cleaved form of PARP is clearly observable on the western blot. An uncleaved band (110 kDa) usually coexists with the cleaved band;

"+++" means that PARP in nearly completely cleaved. The 100 kDa band has often disappeared to the benefit of 85 kDa form.

Apoptotic Nuclear Features:

"+" means a few condensed or fragmented nuclei are observable after DAPI staining;

"++" means that numerous condensed or fragmented nuclei are observable after DAPI staining (20-50%);

"+++" means that most of the nuclei are condensed or fragmented.

---

The invention claimed is:

1. A pharmaceutical composition comprising a compound of formula (I):

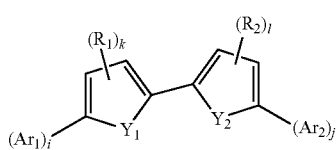

wherein:
$Y_1$, $Y_2$ are —N=C—;
$Ar_1$, $Ar_2$ are each independently selected from $C_6$-$C_{10}$ aryl or a 5 to 7 membered heteroaryl, said aryl and heteroaryl groups being optionally substituted by one to three $R_3$ groups provided that:
  $Ar_1$, $Ar_2$ cannot both identically represent either a 4-pyridyl, an unsubstituted 2 or 3-thiophenyl, or a 3,4-dimethoxyphenyl or a 3,4,5-trimethoxyphenyl,
$R_1$ is selected from, $C_1$-$C_6$ alkyl, $C_6$-$C_{10}$ aryl, ($C_6$-$C_{10}$)aryl($C_1$-$C_6$)alkyl, ($C_6$-$C_{10}$)aryl($C_2$-$C_6$)alkenyl, ($C_6$-$C_{10}$)arylcarbonyl, ($C_6$-$C_{10}$)aryl($C_1$-$C_6$)alkylcarbonyl, C(=O)H, COOH, OH said alkyl groups being optionally substituted by OH;
$R_2$ is selected from ($C_6$-$C_{10}$)aryl($C_1$-$C_6$)alkyl or ($C_6$-$C_{10}$)aryl($C_2$-$C_6$)alkenyl;
k is 0 or 1;
l is 1;
$R_3$ is, at each occurrence, independently selected from $C_1$-$C_6$ alkyl, $C_1$-$C_6$ alkoxy, OH, C(=O)H, $(CH_2)_nCO_2H$, $(CH_2)_pCN$, $(CH_2)_qC(=N(OH))NH_2$, I, Cl, Br, F, $C_6$-$C_{10}$ aryl, and a 5 to 7 membered heteroaryl, ($C_6$-$C_{10}$)aryl($C_1$-$C_6$)alkyl, ($C_6$-$C_{10}$)aryl($C_2$-$C_6$)alkenyl, said alkyl groups being optionally substituted by OH;
n is 0, 1, 2, 3;
p is 0, 1, 2, 3;
q is 0, 1, 2, 3;
with the exclusion of the following compound:
2-(pyridin-3-yl)-5-(5-(pyridin-3-yl)-3-styrylpyridin-2-yl)pyridine;
and the pharmaceutically acceptable salts thereof, in admixture with at least one pharmaceutically acceptable excipient or carrier.

2. The pharmaceutical composition of claim 1, wherein $Ar_1$ and/or $Ar_2$ are selected from phenyl, pyridyl, pyrimidyl, imidazolyl, pyrazolyl, thiophenyl, or triazolyl.

3. The pharmaceutical composition of claim 1, wherein at least one of $Ar_1$, $Ar_2$ is a 5 to 7 membered heteroaryl containing a nitrogen atom.

4. The pharmaceutical composition of claim 2, wherein $Ar_1$ is 3-pyridyl or phenyl.

5. The pharmaceutical composition of claim 2, wherein $Ar_2$ is 3-pyridyl or phenyl.

6. The pharmaceutical composition of claim 1, wherein $R_1$ is selected from $C_1$-$C_6$ alkyl, and $R_2$ is selected from ($C_6$-$C_{10}$)aryl($C_2$-$C_6$)alkenyl.

7. The pharmaceutical composition of claim 1, wherein $R_1$ is 5-methyl.

8. The pharmaceutical composition of claim 1, wherein $R_2$ is 5-styryl.

9. The pharmaceutical composition of claim 1, comprising a structure compound of formula (Ia):

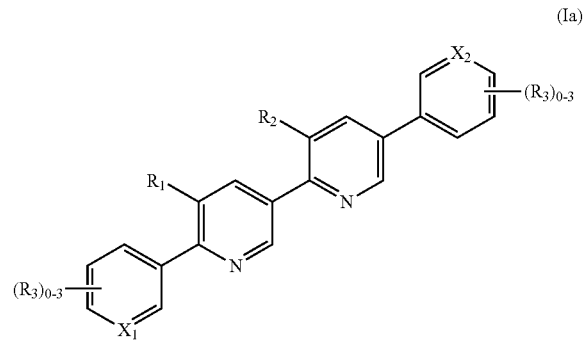

wherein:
$X_1$, $X_2$, are at each occurrence, independently selected from C or N.

10. The pharmaceutical composition of claim 1, wherein the compound of formula (I) is selected from:
5,6'-di(pyridin-3-yl)-5'-methyl-3-((E)-styryl)-2,3'-bipyridine;
5,6"-di(pyridin-3-yl)-3,5"-bis-((E)-styryl)-[2,3';6',3"]terpyridine;

2-(5-methyl-6-(pyridin-3-yl)pyridin-3-yl)-5-phenyl-3-styrylpyridine; or 2-(5-methyl-6-phenylpyridin-3-yl)-5-(pyridin-3-yl)-3-styrylpyridine.

11. The pharmaceutical composition of claim 1, comprising a Bcl$_{-XL}$ inhibitor.

12. A combination comprising a compound of formula (I) according to claim 1, in combination with a Bcl$_{-XL}$ inhibitor.

13. A method for treating cancer, comprising administration of a therapeutically effective amount of a compound of formula (I) to a patient in need thereof, wherein formula (I) is:

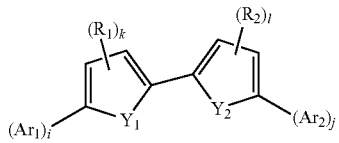

(I)

wherein:

$Y_1$, $Y_2$ are —N=C—;

$Ar_1$, $Ar_2$ are each independently selected from $C_6$-$C_{10}$ aryl or a 5 to 7 membered heteroaryl, said aryl and heteroaryl groups being optionally substituted by one to three $R_3$ groups provided that:

$Ar_1$, $Ar_2$ cannot both identically represent either a 4-pyridyl, an unsubstituted 2 or 3-thiophenyl, or a 3,4-dimethoxyphenyl or a 3,4,5-trimethoxyphenyl;

$R_1$ is selected from, $C_1$-$C_6$ alkyl, $C_6$-$C_{10}$ aryl, ($C_6$-$C_{10}$)aryl($C_1$-$C_6$)alkyl, ($C_6$-$C_{10}$)aryl($C_2$-$C_6$)alkenyl, ($C_6$-$C_{10}$)arylcarbonyl, ($C_6$-$C_{10}$)aryl($C_1$-$C_6$)alkylcarbonyl, C(=O)H, COOH, OH said alkyl groups being optionally substituted by OH;

$R_2$ is selected from ($C_6$-$C_{10}$)aryl($C_1$-$C_6$)alkyl or ($C_6$-$C_{10}$)aryl($C_2$-$C_6$)alkenyl;

k is 0 or 1;

l is 1;

$R_3$ is, at each occurrence, independently selected from $C_1$-$C_6$ alkyl, $C_1$-$C_6$ alkoxy, OH, C(=O)H, $(CH_2)_n CO_2H$, $(CH_2)_p CN$, $(CH_2)_q C(=N(OH))NH_2$, I, Cl, Br, F, $C_6$-$C_{10}$ aryl, and a 5 to 7 membered heteroaryl, ($C_6$-$C_{10}$)aryl($C_1$-$C_6$)alkyl, ($C_6$-$C_{10}$)aryl($C_2$-$C_6$)alkenyl, said alkyl groups being optionally substituted by OH;

n is 0, 1, 2, 3;

p is 0, 1, 2, 3;

q is 0, 1, 2, 3;

with the exclusion of the following compound:

2-(pyridin-3-yl)-5-(5-(pyridin-3-yl)-3-styrylpyridin-2-yl)pyridine;

and a pharmaceutically acceptable salt thereof, in admixture with at least one pharmaceutically acceptable excipient or carrier.

14. The method of claim 13, wherein the compound of formula (I) is administered together with a Bcl$_{-XL}$ inhibitor.

15. The method according to claim 13, wherein the method induces apoptose mediated by Mcl$_{-1}$ protein.

16. A compound of formula (I):

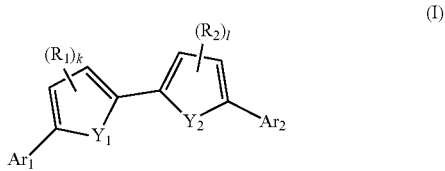

(I)

wherein:

$Y_1$, $Y_2$ are —N=C—;

$Ar_1$, $Ar_2$ are each independently selected from $C_6$-$C_{10}$ aryl or a 5 to 7 membered heteroaryl, said aryl and heteroaryl groups being optionally substituted by one to three $R_3$ groups provided that:

$Ar_1$, $Ar_2$ cannot both identically represent either a 4-pyridyl, an unsubstituted 2 or 3-thiophenyl, or a 3,4-dimethoxyphenyl or a 3,4,5-trimethoxyphenyl;

$R_1$ is selected from, $C_1$-$C_6$ alkyl, $C_6$-$C_{10}$ aryl, ($C_6$-$C_{10}$)aryl($C_1$-$C_6$)alkyl, ($C_6$-$C_{10}$)aryl($C_2$-$C_6$)alkenyl, ($C_6$-$C_{10}$)arylcarbonyl, ($C_6$-$C_{10}$)aryl($C_1$-$C_6$)alkylcarbonyl, C(=O)H, COOH, OH said alkyl groups being optionally substituted by OH;

$R_2$ is selected from ($C_6$-$C_{10}$)aryl($C_1$-$C_6$)alkyl or ($C_6$-$C_{10}$)aryl($C_2$-$C_6$)alkenyl;

k is 0 or 1;

l is 1;

$R_3$ is, at each occurrence, independently selected from $C_1$-$C_6$ alkyl, $C_1$-$C_6$ alkoxy, OH, C(=O)H, $(CH_2)_n CO_2H$, $(CH_2)_p CN$, $(CH_2)_q C(=N(OH))NH_2$, I, Cl, Br, F, $C_6$-$C_{10}$ aryl, and a 5 to 7 membered heteroaryl, ($C_6$-$C_{10}$)aryl($C_1$-$C_6$)alkyl, ($C_6$-$C_{10}$)aryl($C_2$-$C_6$)alkenyl, said alkyl groups being optionally substituted by OH;

n is 0, 1, 2, 3;

p is 0, 1, 2, 3;

q is 0, 1, 2, 3;

with the exclusion of the following compound:

2-(pyridin-3-yl)-5-(5-(pyridin-3-yl)-3-styrylpyridin-2-yl)pyridine and the pharmaceutically acceptable salts thereof.

17. The compound of formula (I) of claim 16, wherein $R_1$ is methyl and $R_2$ is styryl.

18. The compound of formula (I) of claim 17, wherein $R_1$ is 5-methyl and $R_2$ is 5-styryl.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
auuggugagu cggaucgcat t                                                    21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 2
gugccuuugu ggcuaaacat t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gacguaaacg gccacaagut t                                              21
```